(12) United States Patent
Amrutkar et al.

(10) Patent No.: US 10,351,553 B2
(45) Date of Patent: *Jul. 16, 2019

(54) POTASSIUM CHANNEL MODULATORS

(71) Applicant: Cadent Therapeutics, Inc., Cambridge, MA (US)

(72) Inventors: Dipak Vasantrao Amrutkar, Ballerup (DK); Kelly Foster, Watertown, MA (US); Thomas Amos Jacobsen, Oested (DK); Martin R. Jefson, Stonington, CT (US); Gregg F. Keaney, Lexington, MA (US); Janus Schreiber Larsen, Holbæk (DK); Karin Sandager Nielsen, Fredensborg (DK)

(73) Assignee: Cadent Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/938,292

(22) Filed: Mar. 28, 2018

(65) Prior Publication Data
US 2018/0215746 A1  Aug. 2, 2018

Related U.S. Application Data

(63) Continuation of application No. 15/877,910, filed on Jan. 23, 2018, now Pat. No. 9,975,886.
(Continued)

(51) Int. Cl.
*A61K 31/506* (2006.01)
*C07D 413/14* (2006.01)
(Continued)

(52) U.S. Cl.
CPC ........ *C07D 413/14* (2013.01); *A61K 31/5355* (2013.01); *A61P 25/30* (2018.01); *C07D 403/04* (2013.01); *C07D 417/04* (2013.01)

(58) Field of Classification Search
CPC ... A61K 31/506; C07D 417/04; C07D 417/14
(Continued)

(56) References Cited

U.S. PATENT DOCUMENTS 4,992,150 A  2/1991  Igarashi et al.
5,250,530 A  10/1993  Giencke et al.
(Continued)

FOREIGN PATENT DOCUMENTS

CN  101684098 A  3/2010
CN  102731492 A  10/2012
(Continued)

OTHER PUBLICATIONS

Bagal et al., Ion channels as therapeutic targets: a drug discovery perspective. J Med Chem. Feb. 14, 2013;56(3):593-624.
(Continued)

*Primary Examiner* — Jeffrey H Murray
(74) *Attorney, Agent, or Firm* — McCarter & English, LLP; Steven G. Davis; Michael J. DeGrazia

(57) ABSTRACT

Provided herein are compounds of the formula:

(Continued)

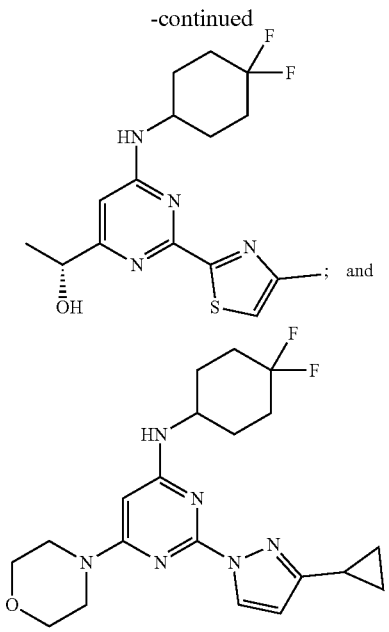

or pharmaceutically acceptable salts thereof, and compositions comprising such compounds for use in the treatment of diseases or conditions responsive to modulation of the small conductance calcium-activated potassium channel (SK channel).

6 Claims, 4 Drawing Sheets

Related U.S. Application Data

(60) Provisional application No. 62/449,270, filed on Jan. 23, 2017.

(51) Int. Cl.
  *A61K 31/5355* (2006.01)
  *C07D 403/04* (2006.01)
  *C07D 417/04* (2006.01)
  *A61P 25/30* (2006.01)

(58) Field of Classification Search
  USPC .................... 514/269, 273; 544/319, 320
  See application file for complete search history.

(56) References Cited

U.S. PATENT DOCUMENTS

| | | | |
|---|---|---|---|
| 6,225,052 B1 | 5/2001 | Batz et al. | |
| 7,767,777 B2 | 8/2010 | Buesing et al. | |
| 7,919,046 B2 | 4/2011 | Delapierre et al. | |
| 8,106,217 B2 | 1/2012 | Ignatyev et al. | |
| 8,222,262 B2 | 7/2012 | Eriksen et al. | |
| 8,252,806 B2 | 8/2012 | Eriksen et al. | |
| 8,362,024 B2 | 1/2013 | Eriksen et al. | |
| 8,563,552 B2 | 10/2013 | Hanyu et al. | |
| 8,586,573 B2 | 11/2013 | Dubois et al. | |
| 9,050,266 B2 | 6/2015 | Poinsard et al. | |
| 9,321,727 B2 | 4/2016 | Bissantz et al. | |
| 9,340,544 B2 | 5/2016 | Eriksen et al. | |
| 9,505,720 B2 | 11/2016 | Poinsard et al. | |
| 9,975,886 B1 * | 5/2018 | Amrutkar | C07D 403/04 |
| 2002/0137747 A1 | 9/2002 | Moriarty et al. | |
| 2004/0229864 A1 | 11/2004 | Bourrain et al. | |
| 2005/0113382 A1 | 5/2005 | Jahangir et al. | |
| 2005/0277640 A1 | 12/2005 | Dixon et al. | |
| 2006/0069066 A1 | 3/2006 | Eldar-Finkelman et al. | |
| 2006/0156481 A1 | 7/2006 | Lim | |
| 2006/0281712 A1 | 12/2006 | Yen et al. | |
| 2007/0135437 A1 | 6/2007 | Benjamin et al. | |
| 2008/0221103 A1 | 9/2008 | Sharma et al. | |
| 2008/0249097 A1 | 10/2008 | Daifuku et al. | |
| 2008/0255183 A1 | 10/2008 | Arnould et al. | |
| 2009/0036475 A1 | 2/2009 | Eriksen et al. | |
| 2009/0068634 A1 | 3/2009 | Cerda | |
| 2009/0143302 A1 | 6/2009 | Yen et al. | |
| 2009/0253717 A1 | 10/2009 | Brown et al. | |
| 2009/0306102 A1 | 12/2009 | Eriksen et al. | |
| 2010/0324273 A1 | 12/2010 | Singer et al. | |
| 2011/0144140 A1 | 6/2011 | Eriksen et al. | |
| 2011/0152292 A1 | 6/2011 | Rayner-Branes et al. | |
| 2011/0224155 A1 | 9/2011 | Tachdjian et al. | |
| 2011/0230484 A1 | 9/2011 | Eriksen et al. | |
| 2011/0257196 A1 | 10/2011 | Lu et al. | |
| 2012/0004246 A1 | 1/2012 | Eriksen et al. | |
| 2012/0046301 A1 | 2/2012 | Frank et al. | |
| 2012/0071524 A1 | 3/2012 | Lu et al. | |
| 2012/0202806 A1 | 8/2012 | Durrenberger et al. | |
| 2013/0197049 A1 | 8/2013 | Li et al. | |
| 2014/0275024 A1 | 9/2014 | Maxwell et al. | |
| 2015/0291515 A1 | 10/2015 | Uerdingen et al. | |
| 2016/0155959 A1 | 6/2016 | Kaiser et al. | |
| 2016/0237069 A1 | 8/2016 | Beaton et al. | |
| 2017/0015871 A1 | 1/2017 | Wutti et al. | |
| 2017/0299609 A1 | 10/2017 | Elbasiouny | |
| 2017/0355708 A1 | 12/2017 | Jefson et al. | |

FOREIGN PATENT DOCUMENTS

| | | |
|---|---|---|
| CN | 103626741 A | 3/2014 |
| CN | 106349156 A | 1/2017 |
| DE | 3634341 A1 | 5/1987 |
| DE | 4034762 A1 | 5/1992 |
| DE | 102012006896 A1 | 10/2013 |
| EP | 353123 A1 | 1/1990 |
| EP | 407899 A2 | 1/1991 |
| EP | 646648 A1 | 4/1995 |
| EP | 1270551 A1 | 1/2003 |
| EP | 1506967 A1 | 2/2005 |
| EP | 2042570 A1 | 4/2009 |
| EP | 2746373 A2 | 6/2014 |
| EP | 2746374 A2 | 6/2014 |
| ES | 2469290 A1 | 6/2014 |
| FR | 2904316 A1 | 2/2008 |
| GB | 2263639 A | 8/1993 |
| JP | 54-147921 A | 11/1979 |
| JP | H02282251 A | 11/1990 |
| JP | H11158073 A | 6/1999 |
| JP | H11282132 A | 10/1999 |
| JP | 2000-072695 A | 3/2000 |
| JP | 2000-075449 A | 3/2000 |
| JP | 2007-091649 A | 4/2007 |
| JP | 2013-020223 A | 1/2013 |
| JP | 2013-061465 A | 4/2013 |
| JP | 2013-125180 A | 6/2013 |
| KR | 20120018236 A | 3/2012 |
| WO | 1989/11279 A1 | 11/1989 |
| WO | 1993/25550 A1 | 12/1993 |
| WO | 1995/00478 A1 | 1/1995 |
| WO | 1998/06709 A1 | 2/1998 |
| WO | 1998/17630 A1 | 4/1998 |
| WO | 2001/017942 A1 | 3/2001 |
| WO | 2001/32170 A1 | 5/2001 |
| WO | 2002/00217 A1 | 1/2002 |
| WO | 2002/030358 A2 | 4/2002 |
| WO | 2002/046172 A2 | 6/2002 |
| WO | 2002/055012 A2 | 7/2002 |
| WO | 2002/055013 A2 | 7/2002 |
| WO | 2002/055014 A2 | 7/2002 |
| WO | 2002/064096 A2 | 8/2002 |
| WO | 2003/053933 A1 | 7/2003 |
| WO | 2003/075828 A2 | 9/2003 |
| WO | 2004/000820 A2 | 12/2003 |

(56) References Cited

FOREIGN PATENT DOCUMENTS

| | | |
|---|---|---|
| WO | 2004/000833 A1 | 12/2003 |
| WO | 2004/017920 A2 | 3/2004 |
| WO | 2004/018452 A1 | 3/2004 |
| WO | 2005/035507 A2 | 4/2005 |
| WO | 2005/037826 A1 | 4/2005 |
| WO | 2005/075461 A1 | 8/2005 |
| WO | 2005/095357 A2 | 10/2005 |
| WO | 2005/112938 A2 | 12/2005 |
| WO | 2006/014136 A1 | 2/2006 |
| WO | 2006/034473 A2 | 3/2006 |
| WO | 2006/040113 A2 | 4/2006 |
| WO | 2006/048330 A1 | 5/2006 |
| WO | 2006/053109 A1 | 5/2006 |
| WO | 2006/065590 A2 | 6/2006 |
| WO | 2006/074057 A2 | 7/2006 |
| WO | 2006/077364 A1 | 7/2006 |
| WO | 2006/077365 A1 | 7/2006 |
| WO | 2006/077366 A1 | 7/2006 |
| WO | 2006/077367 A1 | 7/2006 |
| WO | 2006/077412 A1 | 7/2006 |
| WO | 2006/100212 A1 | 9/2006 |
| WO | 2006/128563 A1 | 12/2006 |
| WO | 2006/138266 A2 | 12/2006 |
| WO | 2007/015064 A1 | 2/2007 |
| WO | 2007/031185 A1 | 3/2007 |
| WO | 2007/042810 A1 | 4/2007 |
| WO | 2007/048924 A1 | 5/2007 |
| WO | 2007/062222 A2 | 5/2007 |
| WO | 2007/070556 A2 | 6/2007 |
| WO | 2007/070600 A2 | 6/2007 |
| WO | 2007/128462 A1 | 11/2007 |
| WO | 2008/005538 A2 | 1/2008 |
| WO | 2008/016300 A2 | 2/2008 |
| WO | 2008/052861 A2 | 5/2008 |
| WO | 2008/064218 A2 | 5/2008 |
| WO | 2008/070661 A1 | 6/2008 |
| WO | 2008/090382 A1 | 7/2008 |
| WO | 2008/098058 A1 | 8/2008 |
| WO | 2008/104994 A2 | 9/2008 |
| WO | 2008/116909 A1 | 10/2008 |
| WO | 2008/116910 A1 | 10/2008 |
| WO | 2008/116911 A1 | 10/2008 |
| WO | 2008/116912 A2 | 10/2008 |
| WO | 2008/116914 A1 | 10/2008 |
| WO | 2008/154221 A2 | 12/2008 |
| WO | 2009/017838 A2 | 2/2009 |
| WO | 2009/099193 A1 | 8/2009 |
| WO | 2009/105881 A1 | 9/2009 |
| WO | 2009/120094 A2 | 10/2009 |
| WO | 2009/125870 A1 | 10/2009 |
| WO | 2009/150462 A1 | 12/2009 |
| WO | 2009/152902 A2 | 12/2009 |
| WO | 2010/000396 A1 | 1/2010 |
| WO | 2010/020432 A2 | 2/2010 |
| WO | 2010/026087 A1 | 3/2010 |
| WO | 2010/034707 A1 | 4/2010 |
| WO | 2010/048149 A2 | 4/2010 |
| WO | 2010/052569 A2 | 5/2010 |
| WO | 2010/068863 A2 | 6/2010 |
| WO | 2010/072823 A1 | 7/2010 |
| WO | 2010/120994 A2 | 10/2010 |
| WO | 2010/129053 A2 | 11/2010 |
| WO | 2010/151711 A1 | 12/2010 |
| WO | 2010/151797 A2 | 12/2010 |
| WO | 2011/004162 A2 | 1/2011 |
| WO | 2011/008931 A2 | 1/2011 |
| WO | 2011/026579 A1 | 3/2011 |
| WO | 2011/026835 A1 | 3/2011 |
| WO | 2011/029832 A1 | 3/2011 |
| WO | 2011/060304 A2 | 5/2011 |
| WO | 2011/077043 A2 | 6/2011 |
| WO | 2011/079343 A2 | 7/2011 |
| WO | 2011/109059 A1 | 9/2011 |
| WO | 2011/143365 A1 | 11/2011 |
| WO | 2012/009258 A2 | 1/2012 |
| WO | 2012/016133 A2 | 2/2012 |
| WO | 2012/022487 A1 | 2/2012 |
| WO | 2012/042005 A1 | 4/2012 |
| WO | 2012/052540 A1 | 4/2012 |
| WO | 2012/080729 A2 | 6/2012 |
| WO | 2012/088438 A1 | 6/2012 |
| WO | 2012/109343 A2 | 8/2012 |
| WO | 2012/129562 A2 | 9/2012 |
| WO | 2012/154880 A1 | 11/2012 |
| WO | 2012/154967 A1 | 11/2012 |
| WO | 2012/163489 A1 | 12/2012 |
| WO | 2012/167171 A2 | 12/2012 |
| WO | 2013/033240 A1 | 3/2013 |
| WO | 2013/120040 A1 | 8/2013 |
| WO | 2013/178816 A1 | 12/2013 |
| WO | 2013/190212 A1 | 12/2013 |
| WO | 2014/017938 A2 | 1/2014 |
| WO | 2014/031681 A1 | 2/2014 |
| WO | 2014/031872 A2 | 2/2014 |
| WO | 2014/045031 A1 | 3/2014 |
| WO | 2014/067603 A1 | 5/2014 |
| WO | 2014/078733 A1 | 5/2014 |
| WO | 2014/107622 A1 | 7/2014 |
| WO | 2014/108487 A1 | 7/2014 |
| WO | 2014/134141 A1 | 9/2014 |
| WO | 2014/165827 A1 | 10/2014 |
| WO | 2015/000548 A1 | 1/2015 |
| WO | 2015/003640 A1 | 1/2015 |
| WO | 2015/011284 A2 | 1/2015 |
| WO | 2015/013715 A2 | 1/2015 |
| WO | 2015/031725 A1 | 3/2015 |
| WO | 2015/049034 A1 | 4/2015 |
| WO | 2015/061247 A2 | 4/2015 |
| WO | 2015/069752 A1 | 5/2015 |
| WO | 2015/079028 A1 | 6/2015 |
| WO | 2015/084936 A1 | 6/2015 |
| WO | 2015/154039 A2 | 10/2015 |
| WO | 2016/058544 A1 | 4/2016 |
| WO | 2016/128772 A1 | 8/2016 |
| WO | 2017/044889 A1 | 3/2017 |
| WO | 2017/210545 A1 | 12/2017 |

OTHER PUBLICATIONS

Kasumu et al., Novel Selective positive modulator of calcium-activated potassium channels exerts beneficial effects in a mouse model of spinocerebellar ataxia type 2. Chem Biol. Oct. 26, 2012;19(10):1340-53.
Nilsson et al., Structural basis for the inhibition of *Mycobacterium tuberculosis* glutamine synthetase by novel ATP-competitive inhibitors. J Mol Biol. Oct. 23, 2009;393(2):504-13.
Copending U.S. Appl. No. 15/617,091, filed Jun. 8, 2017.
Copending U.S. Appl. No. 15/877,910, filed Jan. 23, 2018.
Copending U.S. Appl. No. 15/877,918, filed Jan. 23, 2018.
Copending U.S. Appl. No. 15/749,325, filed Jan. 31, 2018.
U.S. Appl. No. 15/749,325, filed Jan. 31, 2018, Pending.
U.S. Appl. No. 15/617,091, filed Jun. 8, 2017, US 2017-0355708 A1, Published.
U.S. Appl. No. 15/877,910, filed Jan. 23, 2018, Allowed.
U.S. Appl. No. 15/877,918, filed Jan. 23, 2018, Pending.
Cao et al., Modulation of recombinant and native neuronal SK channels by the neuroprotective drug riluzole. Eur J Pharmacol. Aug. 2, 2002;449(1-2):47-54.
Rahimi Shourmasti et al., Effects of riluzole on harmaline induced tremor and ataxia in rats: biochemical, histological and behavioral studies. Eur J Pharmacol. Nov. 15, 2012;695(1-3):40-7.
Addolorato et al., Novel therapeutic strategies for alcohol and drug addiction: focus on GABA, ion channels and transcranial magnetic stimulation. Neuropsychopharmacology. Jan. 2012;37(1):163-77.
Boucherat et al., Potassium channels in pulmonary arterial hypertension. Eur Respir J. Oct. 2015;46(4):1167-77.
Cueni et al., T-type Ca2+ channels, SK2 channels and SERCAs gate sleep-related oscillations in thalamic dendrites. Nat Neurosci. Jun. 2008;11(6):683-92.

(56) References Cited

OTHER PUBLICATIONS

Kanai et al., Altered axonal excitability properties in amyotrophic lateral sclerosis: impaired potassium channel function related to disease stage. Brain. Apr. 2006;129(Pt 4):953-62.

Kobayashi et al., Effects of nicorandil, a potassium channel opener, on idiopathic ventricular tachycardia. J Am Coll Cardiol. Nov. 1998;32(5):1377-83.

Lei et al., Alterations of A-type potassium channels in hippocampal neurons after traumatic brain injury. J Neurotrauma. Jan. 20, 2012;29(2):235-45.

Liu et al., Modulation of the activity of dopaminergic neurons by SK channels: a potential target for the treatment of Parkinson's disease? Neurosci Bull. Jun. 2010;26(3):265-71.

Tano et al., Calcium-activated potassium channels in ischemia reperfusion: a brief update. Front Physiol. Oct. 6, 2014;5:381. 5 pages.

Waszkielewicz et al., Ion channels as drug targets in central nervous system disorders. Curr Med Chem. 2013;20(10):1241-85.

Windler et al., The Ca2+-dependent K+-channel KCa3.1 as a therapeutic target in cardiovascular disease. European Heart Journal Supplements. 2014;16(Suppl A):A30-A32.

Yi et al., Down-regulation of the Small-Conductance Calcium-Activated Potassium Channels in Diabetic Mouse Atria. JBC Papers in Press, published on Jan. 20, 2015 as Manuscript M114.607952, retrieved online at: http://www.jbc.org/cgi/doi/10.1074/jbc.M114.607952. 21 pages, (2015).

Zaki et al., Nicorandil—A Potassium Channel Opener—Ameliorates Overactive Bladder Induced by Type-1 Diabetes in the Male Albino Rats. Med J Cairo Univ. Dec. 2015;83(2):325-332.

\* cited by examiner

*** P<0.005
* P<0.05

POTASSIUM CHANNEL MODULATORS

RELATED APPLICATIONS

This application is a continuation of U.S. Pat. No. 15,877,910, filed Jan. 23, 2018, which claims priority to U.S. Provisional Application No. 62/449,270, filed Jan. 23, 2017, the entire contents of each of which are incorporated herein by reference.

BACKGROUND

Among the ion channels, potassium channels are the most prevalent and diverse, being found in a variety of animal cells such as nervous, muscular, glandular, immune, reproductive, and epithelial tissue. These channels allow the flow of potassium in and/or out of the cell under certain conditions. These channels are regulated, e.g., by calcium sensitivity, voltage-gating, second messengers, extracellular ligands, and ATP-sensitivity.

Dysfunction of potassium channels and dysfunction from other causes which influence these potassium channels are known to generate loss of cellular control, altered physiological function, and disease conditions. Because of their ability to modulate ion channel function and/or regain ion channel activity, potassium channel modulators are being used in the pharmacological treatment of a wide range of pathological diseases and have the potential to address an even wider variety of therapeutic indications.

The small conductance calcium-activated potassium channels (SK channel) are a subfamily of $Ca^{2+}$-activated $K^+$ channels and the SK channel family contains 4 members—SK1, SK2, SK3, and SK4 (often referred to as intermediate conductance). The physiological roles of the SK channels have been especially studied in the nervous system, where for example they are key regulators of neuronal excitability and of neurotransmitter release, and in smooth muscle, where they are crucial in modulating the tone of vascular, broncho-tracheal, urethral, uterine or gastro-intestinal musculature.

Given these implications, small molecule modulators of potassium ion channels could have the potential to treat a large variety of diseases characterized by dysfunction of potassium ion channels and dysfunction from other causes which influence these potassium channels.

SUMMARY

Disclosed are compounds and pharmaceutically acceptable salts thereof, and pharmaceutical compositions thereof, which are useful in the treatment of diseases associated with the dysfunction of potassium ion channels and dysfunction from other causes which influence these potassium channels. (See e.g., Table 1).

The compounds described herein were found to have one or more of the following beneficial properties: high solubility, high brain free fraction, little or no hERG inhibition, extended in vivo half-lives, good bioavailability, high liver microsomal stability, enhanced permeability such as parallel artificial membrane permeability (PAMPA), and/or low Cyp inhibition. See e.g., the comparative data in Tables 2 and 3.

DETAILED DESCRIPTION

1. Compounds

Figure 1:
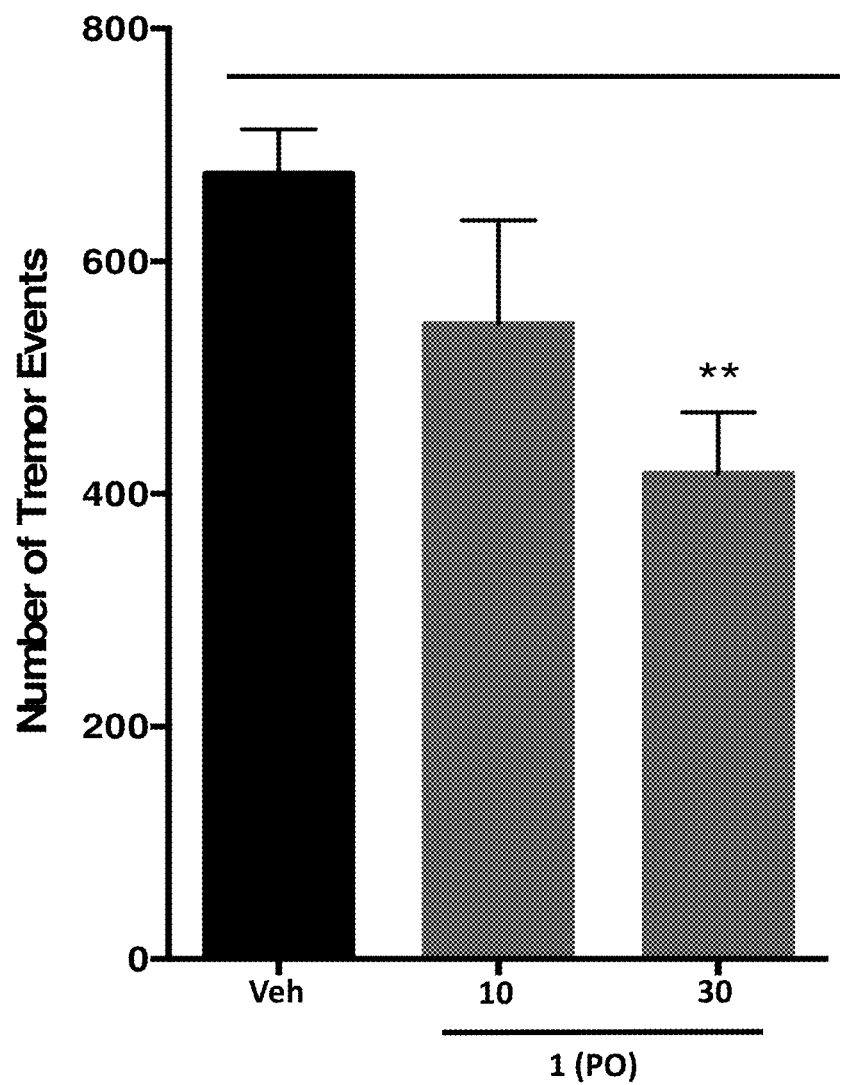
FIG. 1 is a diagram illustrating the effect of Compound 1 following oral (PO) dosing on harmaline induced tremor.

Provided herein are compounds of the formula:

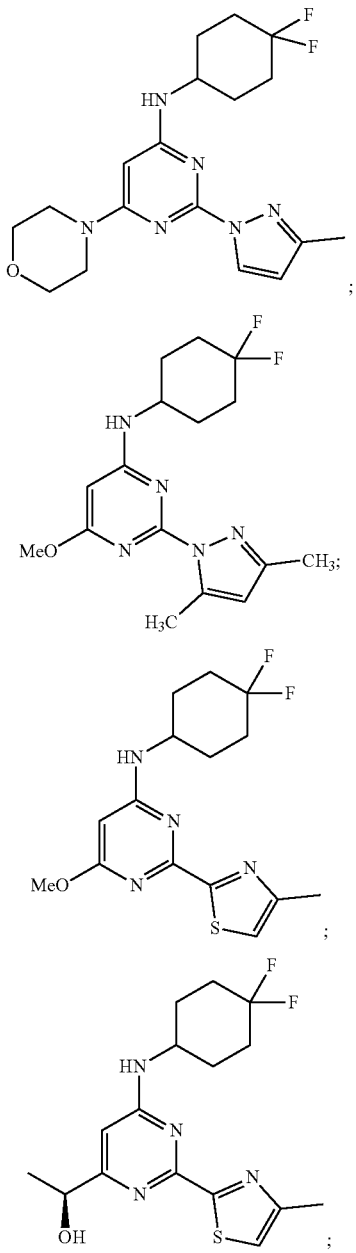

-continued

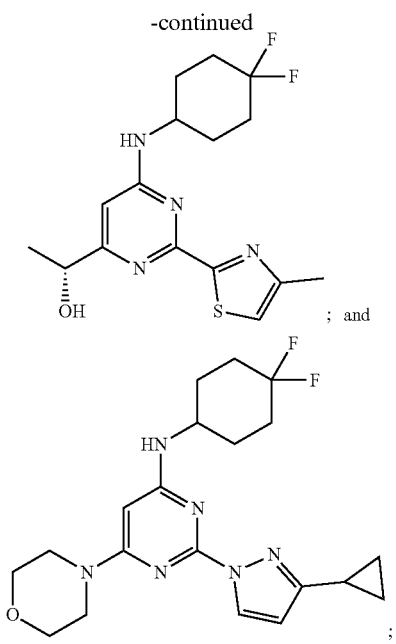

; and or pharmaceutically acceptable salts thereof.

2. Definitions

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisiomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has one chiral center, it is to be understood that the name or structure encompasses one enantiomer of compound free from the corresponding optical and geometric isomer, a racemic mixture of the compound, and mixtures enriched in one enantiomer relative to its corresponding optical isomer.

Pharmaceutically acceptable salts as well as the neutral forms of the compounds described herein are included. For use in medicines, the salts of the compounds refer to non-toxic "pharmaceutically acceptable salts." Pharmaceutically acceptable salt forms include pharmaceutically acceptable acidic/anionic or basic/cationic salts. Pharmaceutically acceptable basic/cationic salts include, the sodium, potassium, calcium, magnesium, diethanolamine, n-methyl-D-glucamine, L-lysine, L-arginine, ammonium, etha- nolamine, piperazine and triethanolamine salts. Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "effective amount" or "therapeutically effective amount" includes an amount of a compound described herein that will elicit a biological or medical response of a subject.

3. Uses, Formulation and Administration

In some embodiments, compounds and compositions described herein are useful in treating diseases and/or disorders associated with the activity of potassium channels. Such diseases and/or disorders include e.g., neurodegenerative and neurological conditions (e.g., Parkinson's disease, tremors, Alzheimer's disease, dementia, amyotrophic lateral sclerosis (ALS) ataxia, anxiety, depression, mood disorders, memory and attention deficits, bipolar disorder, psychosis, schizophrenia, traumatic brain injury, and narcolepsy), heart disease and related conditions (e.g., ischaemic heart disease, coronary heart disease, angina pectoris, and coronary artery spasms), metabolic disease and bladder diseases (e.g., bladder spasms, urinary incontinence, bladder outflow obstruction, gastrointestinal dysfunction, irritable bowel syndrome, and diabetes), withdrawal symptoms associated with termination of addiction, and other conditions associated with the modulation of potassium channels such as e.g., respiratory diseases, epilepsy, convulsions, seizures, absence seizures, vascular spasms, renal disorders (e.g., polycystic kidney disease), erectile dysfunction, secretory diarrhoea, ischaemia, cerebral ischaemia, dysmenorrhea, Reynaud's disease, intermittent claudication, Sjorgren's syndrome, arrhythmia, hypertension, myotonic muscle dystrophia, spasticity, xerostomi, hyperinsulinemia, premature labor, baldness, cancer, immune suppression, migraine and pain.

The present disclosure also provides a method of modulating the activity of a potassium channel in a subject comprising the step of administering a compound described herein. In another embodiment, the present disclosure provides a method of positively modulating a SK2 channel in a cell comprising the step of contacting the cell with a compound described herein.

In one aspect, the provided compounds and compositions are used to treat tremors. Tremors include, but are not limited to rest, active, postural, kinetic, intention, task specific, and idiopathic tremors. In one aspect, the provided compounds and compositions are used to treat postural and active tremors. Examples of postural and/or active tremors include essential tremor, drug-induced parkinsonism, neuropathic tremor, and tremors induced from toxins (e.g., alcohol withdrawal or from exposure to heavy metals). In one aspect, the provided compounds and compositions are used to treat essential tremor.

The present disclosure further provides a method of treating essential tremor in a subject comprising the step of administering a compound or pharmaceutically acceptable salt or composition described herein.

Essential tremor is one of the most common neurological disorders, affecting ~0.9% of the general population. Essential tremor is characterized by an action tremor of the upper limbs and, less commonly, the head, voice, and trunk. A family history of essential tremor can be identified in approximately half of patients, suggesting a genetic component. Drinking alcohol often temporarily reduces tremor.

In some embodiments, the present disclosure provides a method of treating a disease or condition selected from a neurodegenerative disease, dementia, heart disease, withdrawal symptoms associated with termination of addiction, metabolic disease, and bladder disease. In other embodiments, the present disclosure provides a method of treating a disease or condition selected from ataxia, dystonia, Parkinson's disease, ischemia, traumatic brain injury, amyotrophic lateral sclerosis, hypertension, atherosclerosis, diabetes, arrhythmia, over-active bladder, and withdrawal symptoms caused by the termination of abuse of alcohol and other drugs of abuse. In some embodiments, the present disclosure provides a method of treating ataxia. In some embodiments, the present disclosure provides a method of treating spinocerebellar ataxia.

The present disclosure provides pharmaceutically acceptable compositions comprising a compound described herein; and a pharmaceutically acceptable carrier. These compositions can be used to treat one or more of the diseases and conditions described above.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Liquid dosage forms, injectable preparations, solid dispersion forms, and dosage forms for topical or transdermal administration of a compound are included herein.

The amount of provided compounds that may be combined with carrier materials to produce a composition in a single dosage form will vary depending upon the patient to be treated and the particular mode of administration. In some embodiments, provided compositions may be formulated so that a dosage of between 0.01-100 mg/kg body weight/day of the provided compound, such as e.g., 0.1-100 mg/kg body weight/day, can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Exemplification

The representative examples that follow are intended to help illustrate the present disclosure, and are not intended to, nor should they be construed to, limit the scope of the invention.

N-(4,4-difluorocyclohexyl)-2-(3-methyl-1H-pyrazol-1-yl)-6-morpholinopyrimidin-4-amine Step 1:

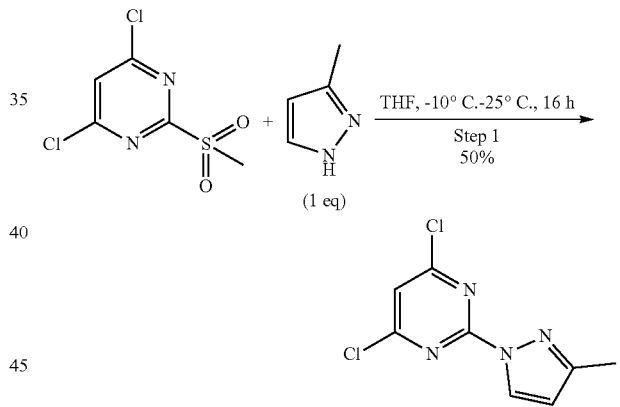

A round-bottomed flask equipped with a teflon-coated stir bar was charged with 4,6-dichloro-2-(methylsulfonyl)pyrimidine (20.0 g, 88.080 mmol, 1.0 eq) in tetrahydrofuran at −10° C. and 3-methyl-1H-pyrazole (7.23 g, 88.080 mmol, 1.0 equiv.) was added dropwise over a period of five minutes via syringe. The reaction mixture was stirred for 16 hours at 25° C. and completion of reaction was determined by TLC. The reaction mixture was portioned between water (500 mL) and ethyl acetate (500 mL). The organic layer was separated and the aqueous layer was extracted with ethyl acetate (2*100 mL). The combined organic layer was dried over sodium sulfate, filtered, and concentrated under reduced pressure to afford crude product which was purified by column chromatography (ethyl acetate/hexane as solvent system) to afford 4,6-dichloro-2-(3-methyl-1H-pyrazol-1-yl)pyrimidine (10.0 g, 43.859 mmol, 50% yield) as a white solid pure form. MS (MH+): m/z=229.1.

Step 2:

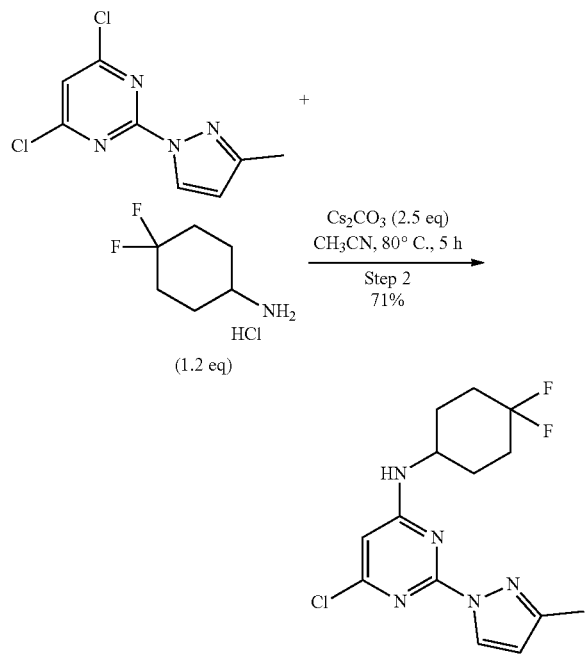

A round-bottomed flask equipped with a teflon-coated stir bar was charged with 2,4-dichloro-6-methylpyrimidine (11.0 g, 48.24 mmol, 1.0 equiv.), 4,4-difluorocyclohexan-1-amine hydrochloride (9.89 g, 57.89 mmol, 1.2 equiv.), and $Cs_2CO_3$ (39.19 g, 120.61 mmol, 2.5 equiv.) in acetonitrile (200 mL). The reaction mixture was stirred for five hours at 80° C. and the completion of reaction was determined by TLC. The reaction mixture was cooled to room temperature and partitioned between water (100 mL) and ethyl acetate (200 mL). The organic layer was separated and the aqueous layer was extracted ethyl acetate (2×100 mL). The combined organic layer was dried over sodium sulfate, filtered, and concentrated under reduced pressure to afford crude product which was purified by column chromatography (ethyl acetate/hexane as solvent system) to afford 6-chloro-N-(4, 4-difluorocyclohexyl)-2-(3-methyl-1H-pyrazol-1-yl)pyrimidin-4-amine (11.0 g, 33.62 mmol, 71%) as an off-white solid. MS (MH+): m/z=328.1.

Step 3:

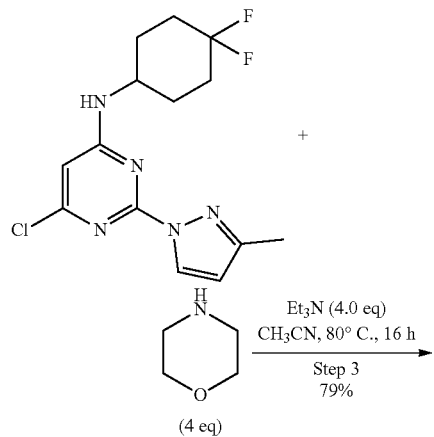

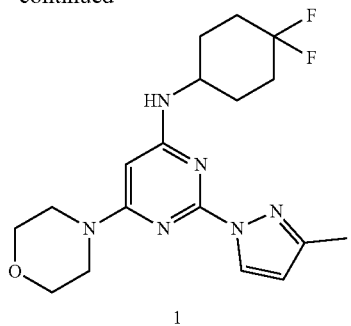

A round-bottomed flask equipped with a teflon-coated stir bar was charged with 6-chloro-N-(4,4-difluorocyclohexyl)-2-(3-methyl-1H-pyrazol-1-yl)pyrimidin-4-amine (14.0 g, 42.79 mmol, 1.0 eq), morpholine (14.91 mL, 171.19 mmol, 4.0 eq), and triethylamine (23.89 mL, 171.19 mmol, 4.0 eq) in acetonitrile (200 mL). The reaction mixture was stirred for 16 hours at 80° C. and completion of reaction was determined by TLC. The reaction mixture was cooled to room temperature and partitioned between water (100 mL) and ethyl acetate (300 mL). The organic layer was separated and the aqueous layer was extracted ethyl acetate (2×100 mL). The combined organic layer was dried over sodium sulfate, filtered, and concentrated under reduced pressure to afford crude product which was purified by column chromatography (ethyl acetate/hexane as solvent system) to afford N-(4,4-difluorocyclohexyl)-2-(3-methyl-1H-pyrazol-1-yl)-6-morpholinopyrimidin-4-amine (1) (12.8 g, 33.84 mmol, 79% yield) as an off-white solid.

Analytical Data:

MS (MH+): m/z=379.2; $^1$H NMR (400 MHz, DMSO-D6): δ 8.41 (d, J=2 Hz, 1H), 7.07 (d, J=8.3 Hz, 1H), 6.25 (d, J=2.4 Hz, 1H), 5.53 (s, 1H), 3.9 (bs, 1H), 3.67 (t, J=4.4 Hz, 4H), 3.49 (S, 4H), 2.23 (s, 3H), 2.23-1.97 (m, 3H), 1.92-1.90 (m, 3H), 1.55-1.53 (m, 2H). $^1$H NMR exhibited, via integration, 3 proton resonances in the aromatic region and 1 broad resonance corresponding to the exchangeable proton at N-18. The aromatic protons were observed as two doublets and a singlet, indicating two adjacent protons, and one isolated aromatic proton. In the aliphatic region, resonances corresponding to 20 protons were observed, showing 1 distinct singlet. Integration of these resonances corresponded to two upfield doublet-doublet resonances, one with a partially overlapping multiplet proton, and four downfield multiplets, two of which partially overlap. The upfield aliphatic multiplets are associated with the morpholine moiety of the structure. The downfield multiplets are split additionally by the proximity of $CF_2$ to these protons. In the high resolution (HR) LC/MS analysis, the pseudomolecular ion (M+H+) was observed at low fragmentor voltage (70V) in ESI positive ion mode at m/z 379.20580. The other prominent ion observed at m/z 779.38575 is attributable to the in-source dimer adduct 2M+Na+.

$^{13}$C NMR data revealed 14 separate carbon resonances and were generated from a decoupled $^{13}$C carbon spectrum acquired at 25° C. in $CDCl_3$. The 14 resonances are consistent with the structure of 1 in which four pairs of the 18 carbons are spectroscopically equivalent. One carbon resonance (C-12 at 77.05 ppm) was observed to be partially obscured by the $CHCl_3$ resonance in the spectrum. The presence of a carbon at this resonance was confirmed by collection of a $^{13}$C spectrum in $C_6D_6$; a resonance at 79.7 ppm was observed without interference from the solvent peak, in addition to all other resonances observed. A triplet (2J=244 Hz) is observed at the C-22 resonance of 122.29, two additional triplets are observed at 31.53 ppm (C-21 & C-23, 3J=24.93 Hz), and at 31.53 ppm (C-20 & C-24, 4J=5.37 Hz). Each of the triplets observed are consistent with F2 substitution at C-22, and decreasing coupling constant with respect to fluorine as the number of intervening bonds increase.

Carbon-proton connectivity, and carbon-carbon connectivity (via 2 and 3-bond C—C—H correlations) of the molecular framework was confirmed by the collection of 2D NMR spectra. Direct C—H connectivity was confirmed by HSQC, and 2- and 3-bond connectivity was demonstrated by HMBC. The short- and long-range cross correlations (over 2 or 3 bonds) are consistent with the connections expected from the proposed structure. Finally, observed chemical shift data assigned as shown above was consistent with computer-predicted $^1$H and $^{13}$C chemical shifts for the proposed structure.

N-(4,4-difluorocyclohexyl)-2-(3,5-dimethyl-1H-pyrazol-1-yl)-6-methoxypyrimidin-4-amine Step 1:

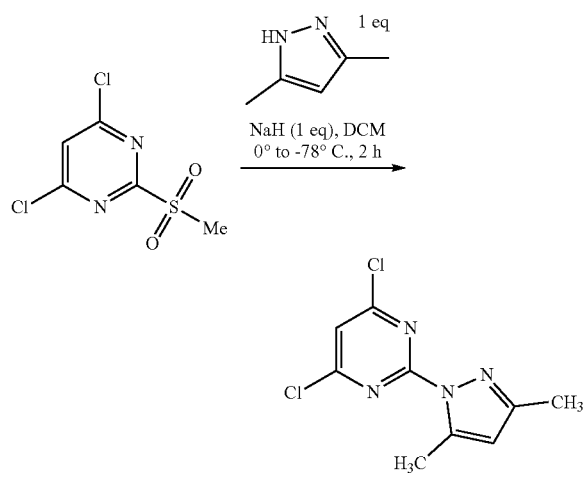

A 5000-mL four-necked, flame-dried, round-bottomed flask, equipped with a teflon-coated stir blade (5 cm) attached with glass rod (neck 1), stopper (neck 2), and addition funnel with stopper (neck 3) and a nitrogen gas inlet-outlet U-tube adaptor filled with oil (Neck 4), was charged with a suspension of sodium hydride (35.2 g, 880 mmol, 1 equiv.) in dichloromethane (1000 mL) was added 3,5-dimethylpyrazole (84.6 g, 880 mmol, 1 equiv.) at 0° C. and the reaction mixture was stirred at room temperature. After 30 min, 4,6-dichloro-2-(methylsulfonyl)pyrimidine (200 g, 880 mmol, 1 equiv.) (dissolved in dichloromethane (1000 mL)) was added dropwise through dropping funnel to the reaction mixture at −78° C. The reaction mixture was stirred at same temperature and the completion of reaction was determined by TLC and UPLC. After 2 h, the reaction mixture was quenched with water at −78° C. and diluted with dichloromethane. After 5 min, dichloromethane was decanted and washed with brine solution. The organic layer was dried over sodium sulfate, filtered, and concentrated under reduced pressure to afford crude product, which was purified by column chromatography using ethyl acetate and pet-ether as solvent to afford 4,6-dichloro-2-(3, 5-dimethyl-1h-pyrazol-1-yl) pyrimidine (138 g, 567.71 mmol, 65%) as an off-white solid. MS (MH+): m/z=244.2.

Step 2:

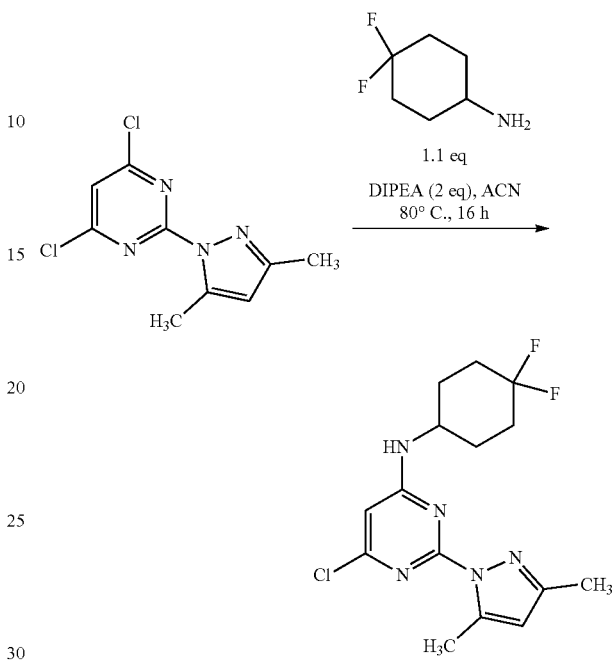

A 2000-mL three-necked, flame-dried, round-bottomed flask, equipped with a teflon-coated stir bar (5 cm), one septa (neck 1), stopper (neck 3) and reflux condenser equipped with nitrogen gas inlet-outlet U-tube adaptor filled with oil (Neck 2), was charged with a solution of 4,6-dichloro-2-(3, 5-dimethyl-1h-pyrazol-1-yl) pyrimidine (136 g, 559.4 mmol, 1 equiv.) in acetonitrile (1500 mL) followed by 4,4-difluorocyclohexylamine hydrochloride (105.6 g, 615.4 mmol, 1.1 equiv.) and N,N-diisopropyl ethylamine (194.88 mL, 1118.8 mmol, 2 equiv). The reaction mixture was heated at 80° C. for 16 h. The completion of reaction was determined by TLC and UPLC. The reaction mixture was concentrated and the residue was triturated with water (500 mL). The resulting solid was filtered, washed with pet-ether, dried under vacuum to afford 6-chloro-N-(4,4-difluorocyclohexyl)-2-(3,5-dimethyl-1h-pyrazol-1-yl)pyrimidin-4-amine (191 g, 556 mmol, >95%) as an off-white solid. MS (MH+): m/z=342.0.

Step 3:

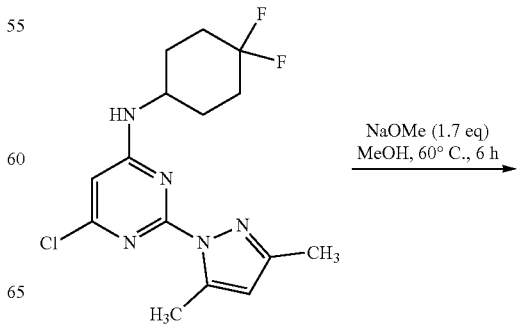

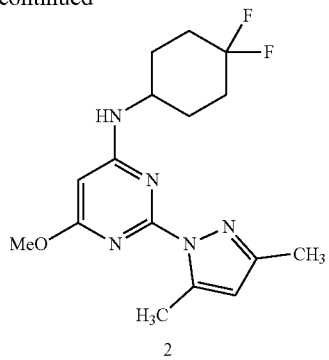

2

A 250 mL three-necked, flame-dried, round-bottomed flask, equipped with a teflon-coated stir bar (2 cm), one septa (neck 1), stopper (neck 3) and reflux condenser equipped with nitrogen gas inlet-outlet U-tube adaptor filled with oil (Neck 2), was charged with a solution of 6-chloro-N-(4,4-difluorocyclohexyl)-2-(3,5-dimethyl-1h-pyrazol-1-yl)pyrimidin-4-amine (20 g, 58.51 mmol, 1 equiv.) in methanol followed by sodium methoxide (21% in methanol, 5.37 g, 99.47 mmol, 1.7 equiv.). The reaction was heated to 60° C., and completion of reaction was determined by TLC and UPLC. After 5 h, the reaction mixture was concentrated under reduced pressure and the residue was diluted with ethyl acetate, washed with water, and washed with brine solution. The organic layer was dried over sodium sulfate, filtered, and concentrated under reduced pressure to afford the crude product which was purified by column chromatography using ethyl acetate in pet-ether as solvent system to afford N-(4,4-difluorocyclohexyl)-2-(3,5-dimethyl-1H-pyrazol-1-yl)-6-methoxypyrimidin-4-amine (2) [16 g (11 g (99% pure)+5 g (92% pure), 47.41 mmol, ~80%) as a white solid. MS (MH+): m/z=338.1. Analytical Data: $^1$H-NMR (400 MHz, DMSO-$d_6$): δ 7.45 (bs, 1H), 6.06 (s, 1H), 5.72 (s, 1H), 4.01 (bs, 1H), 3.85 (s, 3H), 2.55 (s, 3H), 2.17 (s, 3H), 2.11-1.82 (m, 6H), 1.60-1.55 (m, 2H).

N-(4, 4-difluorocyclohexyl)-6-methoxy-2-(4-methylthiazol-2-yl) pyrimidin-4-amine Step 1:

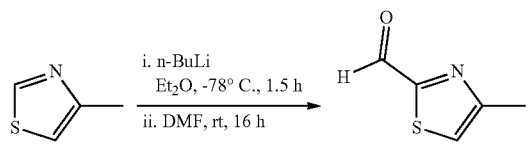

A three-necked round bottomed flask equipped with a teflon-coated stir bar was charged with diethyl ether (250 mL) and n-BuLi (241.98 mL, 604.96 mmol, 2.5M in hexane) was transferred at −78° C. A solution of 4-methylthiazole (50.0 g, 504.13 mmol) in diethyl ether (200 mL) was added over a period of 30 min. The reaction mixture was turned into pale yellow suspension. After 1.5 hours, DMF (58.54 mL, 756.20 mmol) was added and stirred at room temperature for 16 h. The progress of the reaction was monitored by TLC. After completion of the reaction, the mixture was poured into cold aq. HCl (400 mL, 4N) under stirring and separated the two layers. The organic layer was washed with cold aq. HCl (2×80 mL, 4N)). The combined aq. layers were slowly basified with K$_2$CO$_3$ (pH 7) and extracted with diethyl ether (3×150 mL). The combined organic layers were dried over sodium sulfate and evaporated to dryness at room temperature under vacuum to afford 4-methylthiazole-2-carbaldehyde (60.0 g, crude) as a pale yellow liquid. This crude material was used in the next step without further purification.

Step 2:

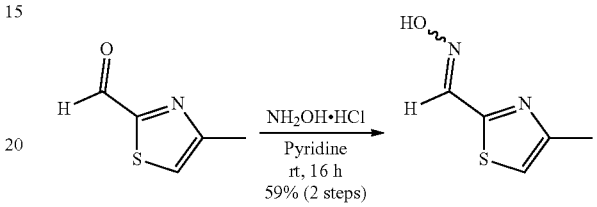

A two-necked round bottomed flask equipped with a teflon-coated stir bar was charged with 4-methylthiazole-2-carbaldehyde (60.0 g, crude) in pyridine (38.04 ml, 472.40 mmol). Hydroxylamine hydrochloride (32.82 g, 472.40 mmol) was added in portions over a period of 15 min. The reaction mixture was stirred at room temperature for 16 h under nitrogen atmosphere. The progress of the reaction was monitored by TLC. After completion of the reaction, the mixture was poured into ice cold water and stirred for 20 min, the obtained solid was filtered and dried under vacuum to afford 4-methylthiazole-2-carbaldehyde oxime (40.0 g, 281.69 mmol, 59% for two steps) as an off white solid. MS (MH+): m/z=143.0.

Step 3:

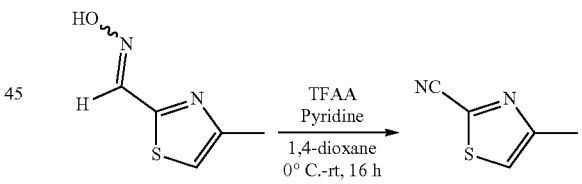

A two-necked round bottomed flask equipped with a teflon-coated stir bar was charged with a solution of 4-methylthiazole-2-carbaldehyde oxime (35.0 g, 246.44 mmol) and pyridine (87.33 mL, 1084.35 mmol) in 1,4-dioxane (140 mL). Trifluoroacetic anhydride (51.38 mL, 369.66 mmol) was added slowly at −10° C. and allowed to stir at room temperature for 16 h. The progress of the reaction was monitored by TLC. After completion of the reaction, the mixture was diluted with water (250 mL) and extracted with diethyl ether (3×350 mL). The combined organic layers were washed with water (2×250 mL), brine (100 mL) dried over sodium sulphate and concentrated under reduced pressure to afford 4-methylthiazole-2-carbonitrile (35.0 g, crude) as light brown liquid. This crude material was used in the next step without further purification. Analytical Data: $^1$H-NMR (400 MHz, DMSO-$d_6$): δ 7.90 (s, 1H), 2.51 (s, 3H).

Step 4:

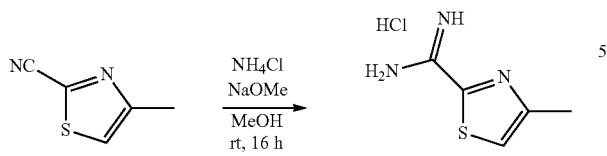

A two-necked round bottomed flask equipped with a teflon-coated stir bar was charged with 4-methylthiazole-2-carbonitrile (35.0 g, crude) in methanol (280 mL) and sodium methoxide (16.77 g, 310.45 mmol) was added. After stirring at room temperature for 3 h, ammonium chloride (30.19 g, 564.66 mmol) was added and stirred for another 16 h. The progress of the reaction was monitored by TLC. After completion of the reaction, the mixture was filtered and washed with methanol. The filtrate was concentrated under reduced pressure and the residue was triturated with diethyl ether (150 mL). The formed solid was filtered and dried under vacuum to afford 4-methylthiazole-2-carboximidamide hydrochloride (35.0 g, crude) as an off-white solid. This crude material was used in the next step without further purification. MS (MH+): m/z=142.0.

Step 5:

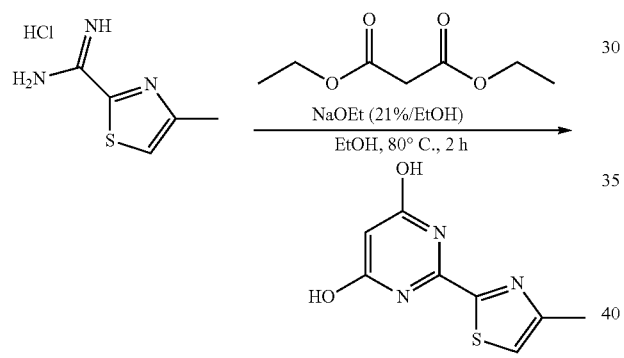

A two-necked round bottomed flask equipped with a teflon-coated stir bar was charged with 4-methylthiazole-2-carboximidamide hydrochloride (35.0 g, crude) in ethanol (350 mL) and diethyl malonate (150.81 mL, 988.64 mmol). Sodium ethoxide (320 mL, 988.64 mmol, 21% in EtOH) was added dropwise at room temperature and heated to 85° C. After 3 hours, the reaction mixture was concentrated under reduced pressure. Water (20 mL) was added and acidified with 1.5 N HCl (pH 2-3). The obtained solid was filtered and dried under vacuum to afford 2-(4-methylthiazol-2-yl) pyrimidine-4, 6-diol (29.0 g, crude) as pale yellow solid. This crude material was used in the next step without further purification. MS (MH+): m/z=210.0.

Step 6:

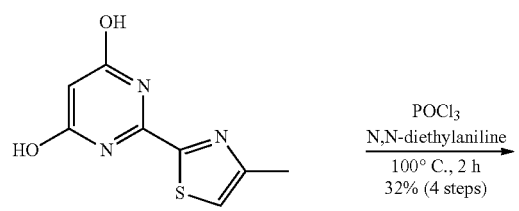

A two-necked round bottomed flask equipped with a teflon-coated stir bar was charged with a suspension of 2-(4-methylthiazol-2-yl) pyrimidine-4, 6-diol (29.0 g, crude) and POCl₃ (290 mL). N,N-diethylaniline (37.84 mL, 235.85 mmol) was added at room temperature and heated reflux at 100° C. for 2 h. The progress of the reaction was monitored by TLC. Excess POCl₃ was removed by distillation. The residue was diluted with 500 mL cold water, neutralized with saturated sodium bicarbonate solution, extracted with diethyl ether (2×500 mL). The combined organic layers were washed with water (3×200 mL), brine (100 mL), dried over sodium sulfate and concentrated under reduced pressure. The residue was triturated with n-pentane (100 mL). The obtained solid was filtered and dried under vacuum to afford 2-(4, 6-dichloropyrimidin-2-yl)-4-methyl-thiazole 7 (19.5 g, 79.59 mmol, 32% for four steps) as a pale yellow solid. MS (MH+): m/z=245.9.

Step 7:

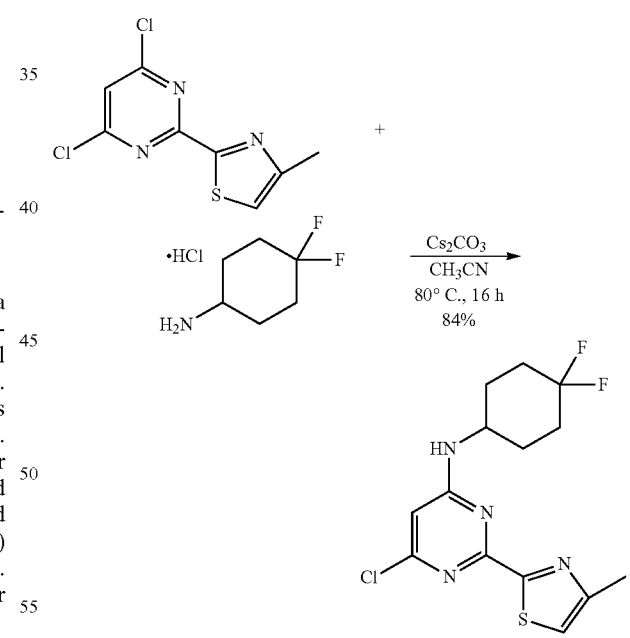

A two necked round bottomed flask equipped with a teflon-coated stir bar was charged with a suspension of 2-(4,6-dichloropyrimidin-2-yl)-4-methylthiazole (19.0 g, 77.56 mmol) and 4, 4-difluorocyclohexan-1-amine hydrochloride (13.30 g, 77.56 mmol) in acetonitrile (190 mL). Cesium carbonate (37.89 g, 116.34 mmol) was added and the reaction mixture was heated at 80° C. for 16 h. The progress of the reaction was monitored by TLC. The reaction mixture was cooled to room temperature, filtered, and the solid was washed with ethyl acetate (500 mL). The filtrate was washed with water (2×100 mL), brine (100 mL), dried over sodium sulfate, and concentrated under reduced pressure. The residue was purified by column chromatography (60-120 silica gel) eluted with 15% EtOAc in hexane. Relevant fractions containing the required compound were combined and evaporated to dryness under reduced pressure to afford 6-chloro-N-(4,4-difluorocyclohexyl)-2-(4-methylthiazol-2-yl)pyrimidin-4-amine (22.5 g, 65.25 mmol, 84%) as off-white foam solid. MS (MH+): m/z=344.9.

Step 8:

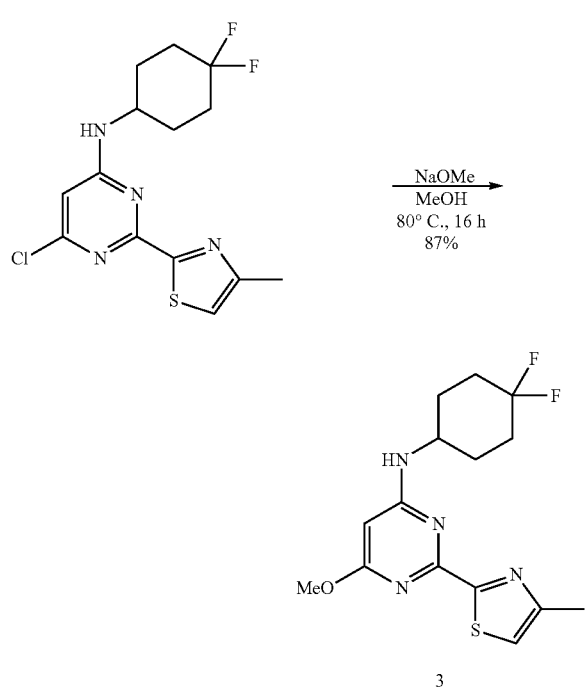

A two-necked round bottomed flask equipped with a teflon-coated stir bar was charged with 6-chloro-N-(4, 4-difluorocyclohexyl)-2-(4-methylthiazol-2-yl) pyrimidin-4-amine (27.0 g, 78.47 mmol) in methanol (450 mL). Sodium methoxide (21.19 g, 392.36 mmol) was added and heated to 80° C. for 16 h. The progress of the reaction was monitored by TLC. Excess methanol was removed under reduced pressure and the residue was diluted with 10% aqueous ammonium chloride solution (100 mL) and extracted with ethyl acetate (3×150 mL). The combined organic layers were washed with water (2×100 mL), brine (100 mL), dried over sodium sulphate and concentrated under reduced pressure. The residue was purified by column chromatography (60-120 silica gel) eluting with 35-40% of EtOAc in hexane. Relevant fractions containing the target compound were combined and evaporated to dryness under reduced pressure to afford N-(4, 4-difluorocyclohexyl)-6-methoxy-2-(4-methylthiazol-2-yl) pyrimidin-4-amine (3) (23.4 g, 68.82 mmol, 87%) as an off-white solid. MS (MH+): m/z=341.0. Analytical Data: $^1$H-NMR (400 MHz, DMSO-d$_6$): δ 7.41 (s, 1H), 7.40 (s, 1H), 5.81 (s, 1H), 3.87 (s, 3H), 2.43 (s, 3H), 2.08-1.89 (m, 6H), 1.61-1.52 (m, 2H).

(S)-1-(6-((4,4-difluorocyclohexy)amino)-2-(4-methylthiazol-2-yl)pyrimidin-4-yl)ethan-1-ol Step 1:

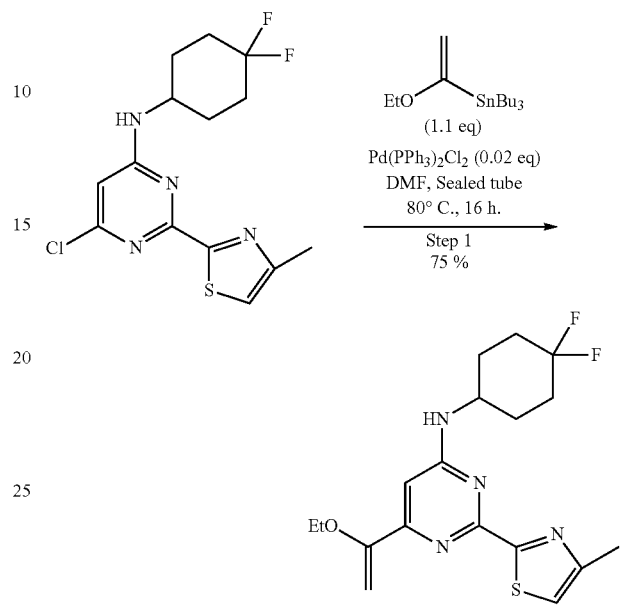

A 250-mL sealed tube, equipped with a teflon-coated stir bar (2 cm), was charged with a solution of 6-chloro-N-(4,4-difluorocyclohexyl)-2-(4-methylthiazol-2-yl)pyrimidin-4-amine (4.9 g, 14.24 mmol, 1.0 eq) and tributyl(1-ethoxyvinyl)stannane (5.65 g, 15.66 mmol, 1.1 eq) in N,N-dimethylformamide (60 mL). The reaction mixture was degassed using argon gas for 5-10 min, followed by addition of bis(triphenylphosphine)palladium(II) dichloride (0.2 g, 0.28 mmol, 0.02 eq). The reaction mixture was sealed and heated at 80° C. for 16 h (completion of reaction was determined by LCMS) and cooled to room temperature. The reaction mixture was diluted with water (300 mL) and extracted with ethyl acetate (2×150 mL). The combined organics were dried over sodium sulfate, filtered, and evaporated to afford a crude product as a light brown sticky solid. The crude material was purified by column chromatography (ethyl acetate/hexane as solvent system) to afford N-(4,4-difluorocyclohexyl)-6-(1-ethoxyvinyl)-2-(4-methylthiazol-2-yl)pyrimidin-4-amine (4.1 g, 10.78 mmol, 75%) as an off-white solid. MS (MH+): m/z=381.0.

Step 2:

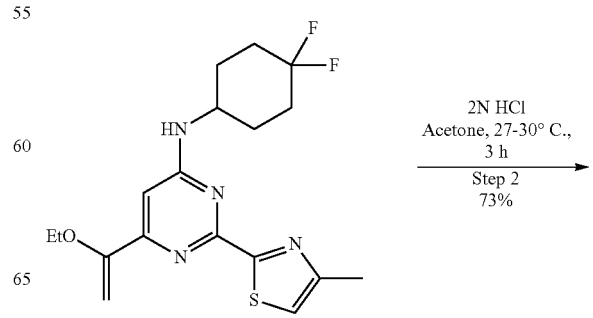

-continued

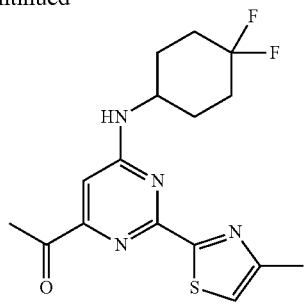

A round-bottomed flask equipped with a teflon-coated stir bar was charged with N-(4,4-difluorocyclohexyl)-6-(1-ethoxyvinyl)-2-(4-methylthiazol-2-yl)pyrimidin-4-amine (9.0 g, 23.67 mmol, 1.0 eq) in acetone (120 mL) followed by addition of 2N hydrochloric acid aqueous solution (20 mL). The reaction mixture was stirred at room temperature for 3 hours and completion of reaction was determined by LCMS. The reaction mixture was concentrated to remove acetone, diluted with ice cold water (100 mL), basified with saturated sodium by carbonate solution, and extracted with ethyl acetate (2×100 mL). The combined organics were dried over sodium sulfate, filtered, and evaporated under reduced pressure to afford a crude product as a light brown sticky solid. The crude material was purified by column chromatography (ethyl acetate/hexane as solvent system) to afford 1-(6-((4, 4-difluorocyclohexyl)amino)-2-(4-methylthiazol-2-yl)pyrimidin-4-yl)ethan-1-one (6.1 g, 17.32 mmol, 73%) as an off-white solid. MS (MH+): m/z=353.0.

Step 3:

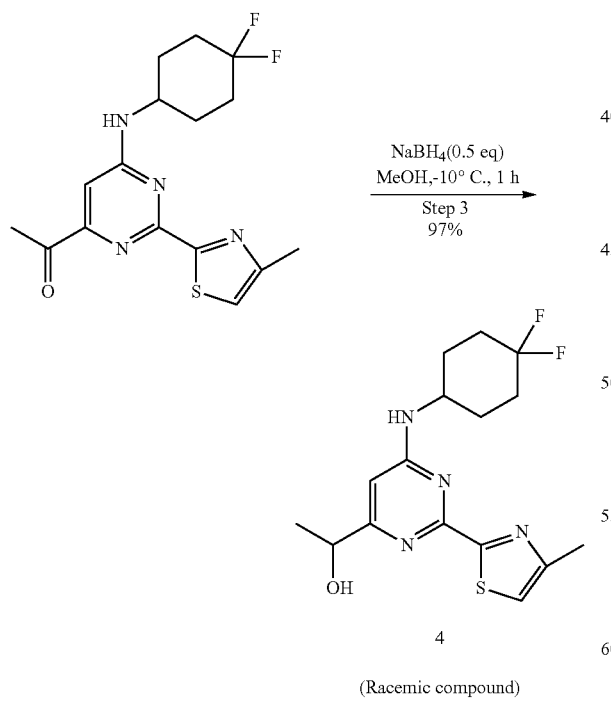

A round-bottomed flask equipped with a teflon-coated stir bar was charged with 1-(6-((4,4-difluorocyclohexyl)amino)-2-(4-methylthiazol-2-yl)pyrimidin-4-yl)ethan-1-one (5.6 g, 15.90 mmol, 1.0 eq) in methanol (80 mL) at −10° C. followed by sodium borohydride (0.302 g, 7.95 mmol, 0.5 eq). The reaction mixture was stirred at same temperature for 1 hour and completion of reaction was determined by LCMS. The reaction mixture was quenched with water and concentrated under reduced pressure to remove methanol. The residue was diluted with ice cold water (100 mL) and extracted with ethyl acetate (2×100 mL). The combined organics were dried over sodium sulfate, filtered, and evaporated under reduced pressure to afford 1-(6-((4,4-difluorocyclohexyl)amino)-2-(4-methylthiazol-2-yl)pyrimidin-4-yl)ethan-1-ol 4 (5.5 g, 15.53 mmol, 97%) as an off-white solid of racemic mixture. MS (MH+): m/z=355.0.

Step 4:

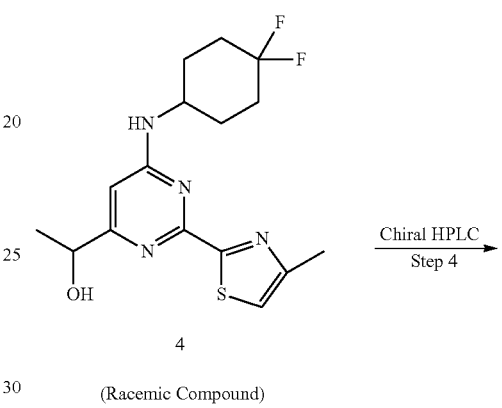

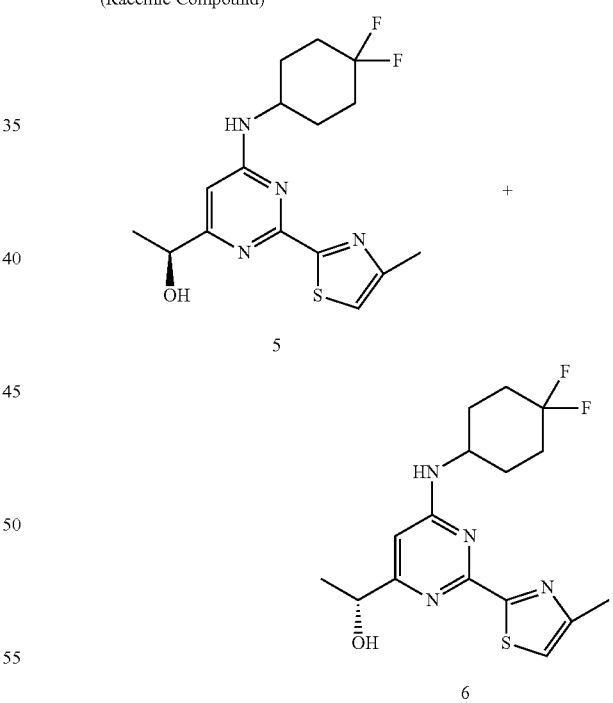

The racemic compound 1-(6-((4,4-difluorocyclohexyl)amino)-2-(4-methylthiazol-2-yl)pyrimidin-4-yl)ethan-1-ol 4 (5.5 g) was purified by chiral HPLC (Column: Chiralpak-IC (250*20*5.0μ); Mobile phase-A:N-Hexane (0.1% DEA), Mobile phase-B: IPA:DCM (90:10) isocratic: 50:50 (A:B); Flow rate: 15.0 ml/min; 120/inj; Run time: 15 min) to afford (S)-1-(6-((4,4-difluorocyclohexyl)amino)-2-(4-methylthiazol-2-yl)pyrimidin-4-yl)ethan-1-ol 5 (2.1 g, 5.93 mmol, 38%) as an off-white solid from first eluting fractions (Peak-1, RT=4.24 min.). MS (MH+): m/z=355.0. ¹H NMR (400 MHz, DMSO-d₆): δ 7.59-7.57 (d, J=6.0 Hz, 1H), 7.37 (s, 1H), 6.64 (s, 1H), 5.37-5.36 (d, J=4.4 Hz, 1H), 4.52-4.50 (t, J=11.2 Hz, 5.6 Hz, 1H), 4.05 (bs, 1H), 2.43 (s, 3H), 2.10-1.96 (m, 6H), 1.62-1.59 (m, 2H), 1.35-1.33 (d, J=6.4 Hz, 3H). Other enantiomer: (R)-1-(6-((4,4-difluorocyclohexyl)amino)-2-(4-methylthiazol-2-yl)pyrimidin-4-yl) ethan-1-ol 6 (2.05 g, 5.78 mmol, 37%) as an off-white solid from second eluting fractions (Peak-2, RT=6.45 min.). MS (MH+): m/z=355.0. ¹H NMR (400 MHz, DMSO-d₆): δ 7.60-7.59 (d, J=5.6 Hz, 1H), 7.37 (s, 1H), 6.64 (s, 1H), 5.38 (bs, 1H), 4.52-4.51 (d, J=6.8 Hz, 1H), 4.10 (bs, 1H), 2.43 (s, 3H), 2.10-1.91 (m, 6H), 1.65-1.57 (m, 2H), 1.35-1.34 (d, J=6.8 Hz, 3H).

2-(3-cyclopropyl-1H-pyrazol-1-yl)-N-(4,4-difluorocyclohexyl)-6-morpholinopyrimidin-4-amine Step 1:

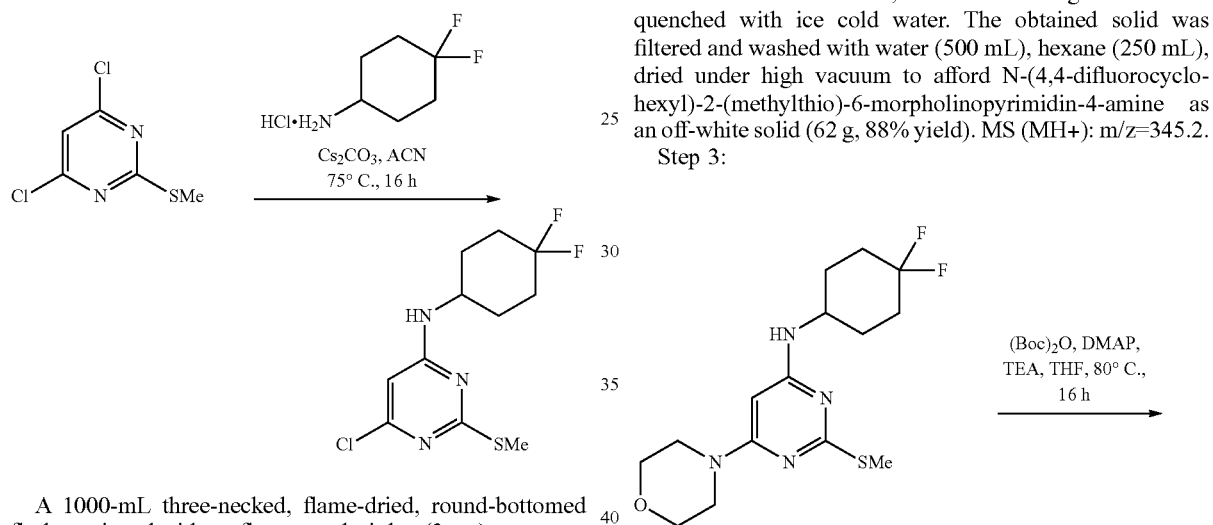

A 1000-mL three-necked, flame-dried, round-bottomed flask, equipped with a teflon-coated stir bar (3 cm), one septa (neck 1), stopper (neck 3) and reflux condenser equipped with nitrogen gas inlet-outlet U-tube adaptor filled with oil (Neck 2), was charged with a solution of 4,6-dichloro-2-(methylthio)pyrimidine (150 g, 768.94 mmol, 1.0 equiv.) in acetonitrile (1500 mL) followed by 4,4-difluorocyclohexylamine hydrochloride (158.35 g, 922.733 mmol) and cesium carbonate (526 g, 1614 mmol, 2.1 equiv.). The reaction mixture was heated at 75° C. for 16 h. The reaction mixture was filtered to remove cesium carbonate, then the filtrate was concentrated under reduced pressure to afford 210 g (93% yield) of 6-chloro-N-(4,4-difluorocyclohexyl)-2-(methylthio)pyrimidin-4-amine as a pale yellow solid. MS (MH+): m/z=294.0.

Step 2:

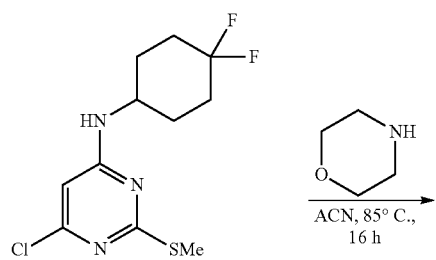

A solution of 6-chloro-N-(4, 4-difluorocyclohexyl)-2-(methylthio)pyrimidin-4-amine (60 g, 204.24 mmol, 1.0 equiv.) and morpholine (35.6 mL, 408.48 mmol, 2.0 equiv.) in acetonitrile (600 mL) was heated at 85° C. in a sealed tube for 16 h. After completion of the reaction, the reaction mixture was concentrated, and the resulting residue was quenched with ice cold water. The obtained solid was filtered and washed with water (500 mL), hexane (250 mL), dried under high vacuum to afford N-(4,4-difluorocyclohexyl)-2-(methylthio)-6-morpholinopyrimidin-4-amine as an off-white solid (62 g, 88% yield). MS (MH+): m/z=345.2.

Step 3:

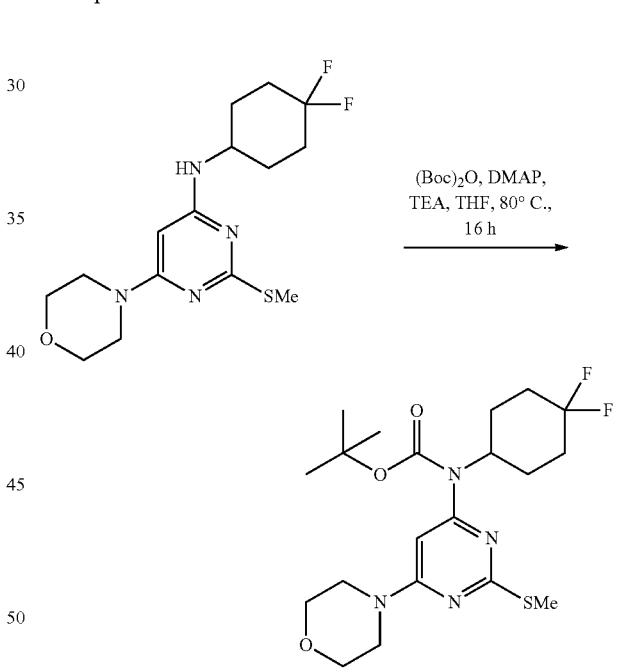

A 100-mL three-necked, flame-dried, round-bottomed flask, equipped with a teflon-coated stir bar (3 cm), one septa (neck 1), stopper (neck 3) and reflux condenser equipped with nitrogen gas inlet-outlet U-tube adaptor filled with oil (Neck 2), was charged with a solution of N-(4,4-difluorocyclohexyl)-2-(methylthio)-6-morpholino pyrimidin-4-amine (1 g, 2.90 mmol) in tetrahydrofuran (15 mL) followed by 4-N,N-dimethylaminopyridine (0.1 g, 0.87 mmol, 0.3 equiv.), triethylamine (1.2 mL, 8.71 mmol, 3.0 equiv.) and Boc anhydride (3.16 g, 14.51 mmol, 5.0 equiv.) then the reaction mixture was heated at 80° C. for 16 h. After completion of the reaction, the reaction mixture was quenched with water and extracted with ethyl acetate (2×75 mL). The combined organic layer was dried over anhydrous sodium sulfate and concentrated to afford tert-butyl (4,4-difluorocyclohexyl)(2-(methylthio)-6-morpholino pyrimidin-4-yl)carbamate as a yellow gum (1.1 g, 85%). MS (MH+): m/z=445.2.

Step 4:

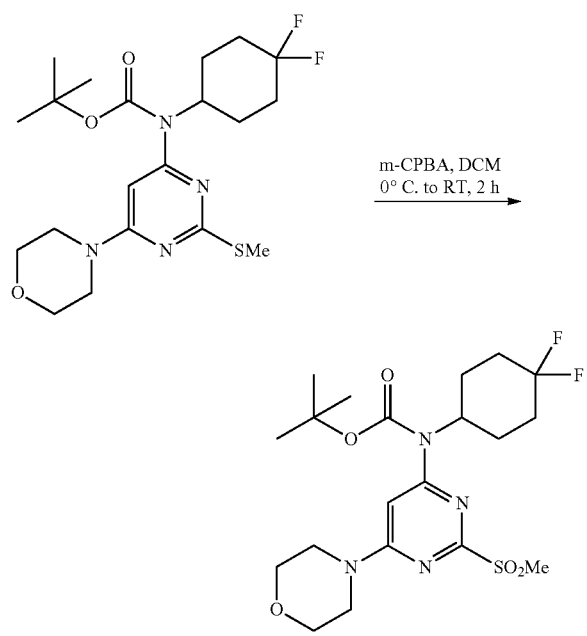

A 100-mL single neck round bottom flask, connected with reflux condenser equipped with nitrogen gas inlet-outlet U-tube adaptor filled with oil, a teflon-coated stir bar (1 cm), was charged with a solution of tert-butyl (4,4-difluorocyclohexyl)(2-(methylthio)-6-morpholinopyrimidin-4-yl)carbamate (50 g, 112.47 mmol) in dichloromethane (600 mL) followed by 3-chloroperbenzoic acid (m-chloroperbenzoic acid) (58.2 g, 337.42 mmol, 3.0 equiv.) at 0° C. The reaction mixture was slowly warmed to rt and stirred for 30 min. After the completion of the reaction, the reaction mixture was quenched with saturated bicarbonate solution and extracted with dichloromethane (2×250 mL). The combined organic layer was dried over anhydrous sodium sulfate and concentrated to afford tert-butyl (4,4-difluorocyclohexyl)(2-(methylsulfonyl)-6-morpholinopyrimidin-4-yl)carbamate as an off-white gum (52 g, 97% yield). MS (MH+): m/z=477.3.

Step 5:

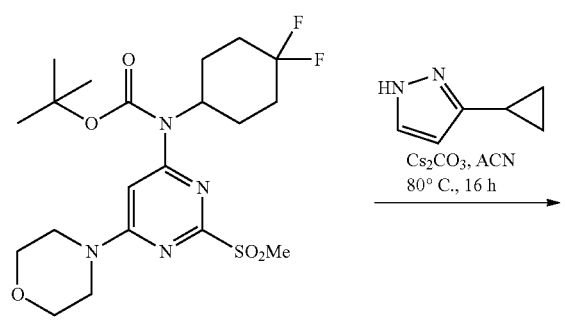

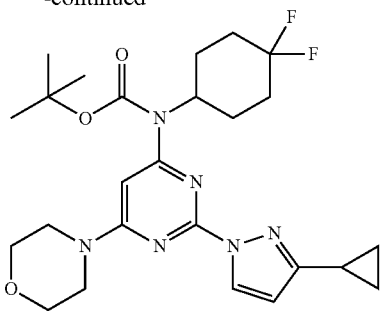

A 100-mL single neck round bottom flask, connected with reflux condenser equipped with nitrogen gas inlet-outlet U-tube adaptor filled with oil, a teflon-coated stir bar (2 cm), was charged with a solution of tert-butyl (4,4-difluorocyclohexyl)(2-(methylsulfonyl)-6-morpholinopyrimidin-4-yl) carbamate (0.9 g, 1.88 mmol) in acetonitrile (10 mL) followed by 3-cyclopropyl-1H-pyrazole (0.3 g, 2.83 mmol, 1.5 equiv.) and cesium carbonate (1.23 g, 3.77 mmol, 2.0 equiv.). The reaction mixture was heated at 80° C. for 16 hours, and completion of reaction was determined by TLC and LCMS. The reaction mixture was filtered and the filtrate was concentrated. The crude product was purified through column chromatography using 60-120 silica gel with ethyl acetate-pet ether as solvent system. The isolated material was dried under vacuum to afford tert-butyl (2-(3-cyclopropyl-1H-pyrazol-1-yl)-6-morpholinopyrimidin-4-yl)(4,4-difluorocyclohexyl)carbamate as an off-white solid (0.8 g, 84%). MS (MH+): m/z=505.

Step 6:

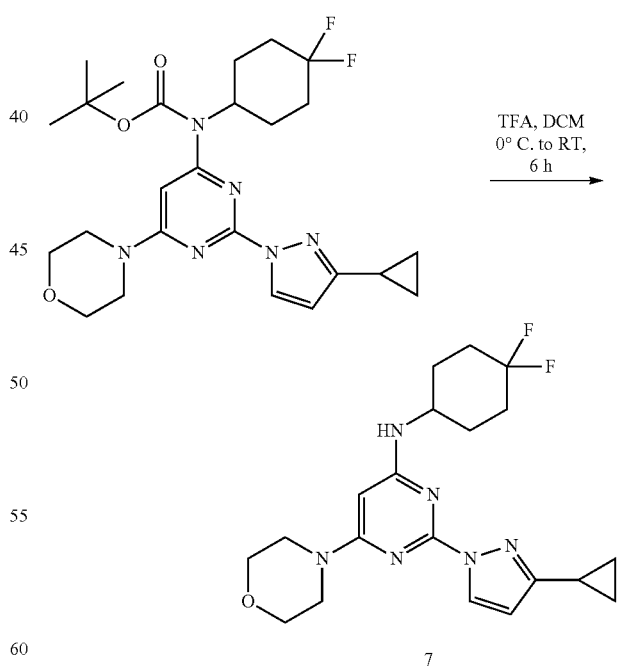

A 100-mL three-necked, flame-dried, round-bottomed flask, equipped with a teflon-coated stir bar (2 cm), one septa (necks 1), stopper (neck 3) and nitrogen gas inlet-outlet U-tube adaptor filled with oil (Neck 2), was charged with a solution tert-butyl (2-(3-cyclopropyl-1H-pyrazol-1-yl)-6- morpholinopyrimidin-4-yl)(4,4-difluorocyclohexyl)carbamate (1.2 g, 1.98 mmol, 1 eq) in dichloromethane (40 mL) followed by trifluoroacetic acid (2.5 mL, 32.55 mmol, 16.4 eq) at 0° C. The reaction mixture was slowly warmed to rt and stirred at same temperature for 6 hours. The completion of reaction was determined by TLC and UPLC. The reaction mixture was concentrated and the resulting residue was quenched with 10% saturated sodium bicarbonate solution, extracted with ethyl acetate (2×100 mL), and concentrated under reduced pressure to afford crude product. The crude product was purified through column chromatography using 60-120 silica gel, ethyl acetate-pet ether as solvent system. The resulting solid was dried under vacuum to afford 2-(3-cyclopropyl-1H-pyrazol-1-yl)-N-(4,4-difluorocyclohexyl)-6-morpholinopyrimidin-4-amine 7 (0.73 g, 90%). MS (MH+): m/z=405. Analytical Data: $^1$H-NMR (400 MHz, DMSO-$d_6$): δ 8.39 (d, J=2.4 Hz, 1H), 7.08 (d, J=8.0 Hz, 1H), 6.14 (d, J=2.80 Hz, 1H), 5.53 (s, 1H), 3.88 (s, 1H), 3.69-3.67 (m, 4H), 3.50 (m, 4H), 1.99-1.90 (m, 7H), 1.56-1.54 (m, 2H), 0.93-0.89 (m, 2H), 0.72-0.71 (m, 2H).

Biological Assays

The biological activity was determined as follows. The ionic current through small-conductance $Ca^{2+}$-activated $K^+$ channels (SK channels, subtype 2) was measured using the whole-cell configuration of the patch-clamp technique in a patch-clamp set-up using HEK293 tissue culture cells expressing SK2 channels as described in Hougaard et al., British Journal of Pharmacology 151, 655-665, May 8, 2007, the entire teachings of which are incorporated herein by reference. In one aspect, a compound is defined to be an SK Positive Allosteric Modulator (PAM) if the compound increases current in this assay, for example, if the $SC_{100}$ value of the compound is less than or equal to 10 µM as determined by this assay. The $SC_{100}$ value is defined to be the concentration of compound that increases the basal current by 100%.

The $SC_{100}$ value is given in Table 1.

Male Sprague Dawley rats were administered with either Vehicle, 10, or 30 mg/Kg Compound 1 by oral administration 30 minutes prior to harmaline injection to investigate the therapeutic effect of Compound 1 on harmaline induced tremor. Immediately following harmaline injection, animals were placed in the tremor quantification apparatus and tremor events were quantified for 60 minutes. A tremor event signal was generated when a small metal transmitter band fitted to the right forepaw of the animal moved within the electromagnetic field generated by a loop antenna within the testing apparatus. Outputs from the amplifier were digitized at a sampling rate of 1,000 Hz and the signal was processed and analyzed using LabView software (National Instruments). To minimize signal from ambulatory and grooming behavior, the signal was filtered with a 128-ms unweighted moving average filter, and events with amplitudes>0.5 V and lasting>300 ms in duration were counted as a tremor event. Data were analyzed in one-minute bins over the course of the test and presented as the sum of tremor events over the entire 60 minute test. As shown by FIG. 1, significant inhibition of tremors was observed at a dose of 30 mg/Kg Compound 1.

Reduction of tremor with Compound 1 has also been demonstrated by measurement of whole-body tremor frequency via a force-plate accelerometer.

Figure 2:
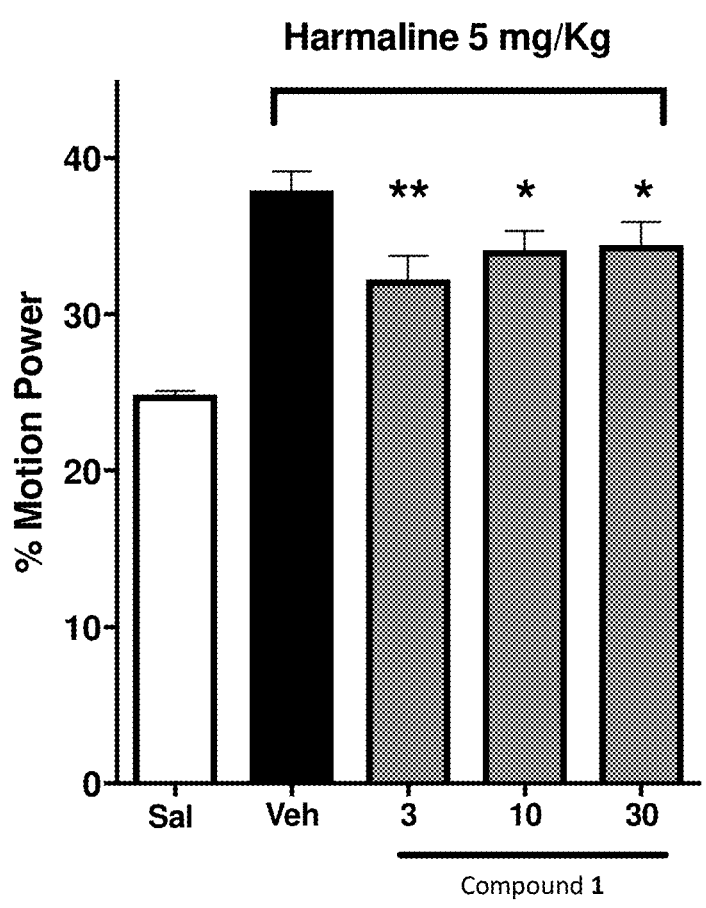
FIG. 2 displays the efficacy and dose response of Compound 1 in percent motion power.

Whole body tremor was measured by a San Diego Instruments Tremor Monitor (San Diego, Calif., USA). Animals were pre-treated with 3, 10, or 30 mg/kg Compound 1 orally 30 minutes prior to intraperitoneal administration of 5 mg/kg harmaline. Tremor was measured for 30 minutes following harmaline administration, and data were analyzed by fast Fourier transform and reported as a frequency power spectrum. Harmaline induced a significant increase in the power spectrum in a band of frequencies between 10 and 14 Hz. In this range, 3, 10, and 30 mg/kg all significantly reduced tremor. Data were further analyzed by calculating the percent Motion Power (% MP), defined as the power in the 9-13 Hz band divided by the total power across the spectrum (0-30 Hz) multiplied by 100. By this analysis, 3, 10, and 30 mg/kg significantly reduced harmaline-induced tremor (harmaline+vehicle (n=13); harmaline+3 mg/kg Compound 1 (n=8), P<0.01; 10 mg/kg Compound 1 (n=16) and 30 mg/kg Compound 1 (n=13), respectively, P<0.05) (FIG. 2).

Taken together, these data show that Compound 1 significantly reduces harmaline-induced tremor measured by two different experimental designs.

The extent to which compounds modulate SK2 channels in vivo is expressed as % SK2 $SC_{100}$, which is the ratio of the concentration of the drug free in the brain to the measured potency of the compound on the SK2 channel. It is calculated as follows: $C_{FB}=C_{MB} \times BFF$, where $C_{MB}$ is the concentration of compound measured by liquid chromatography mass spectrometry from brains harvested immediately following tremor recording (Table 1, "Measured Brain Concentration"). $C_{FB}$ is the amount of free compound not complexed with protein and therefore free to interact with the SK2 channel (Table 1, "Calculated Free Brain Concentration"). BFF is average free fraction of compound as measured by equilibrium dialysis in separate experiments (1 uM test concentration incubated in 10% rat brain tissue homogenate for 5 hours at 37° C.) (Table 1, "Brain Free Fraction"). Free drug in brain available to interact with SK2 channels ($C_{FB}$) is arrived at by multiplying the measured total brain level ($C_{MB}$) by the average free fraction (BFF).

The amount of free compound is then expressed in terms of its potency against the SK2 channel as follows: % SK2 $SC_{100}=C_{FB}/SK2\ SC_{100} \times 100$, where SK2 $SC_{100}$ (Table 1, "SK2 $SC_{100}$") is the measured value of potency of the compound on SK2 channels and % SK2 $SC_{100}$ (Table 1, "% SK2 $SC_{100}$") is the free brain concentration ($C_{FB}$) normalized to SK2 $SC_{100}$. Values are given in Table 1.

TABLE 1

| Compound | Minimally Efficacious Dose (mg/Kg) | Measured Brain Concentration (µM) | Measured Brain Free Fraction | Calculated Free Brain Concentration (µM) | Measured SK2 $SC_{100}$ (µM) | Calculated % SK2 $SC_{100}$ |
|---|---|---|---|---|---|---|
| 1 | 30 | 1.3 | 0.065 | 0.08 | 0.5 | 16 |

Figure 3:
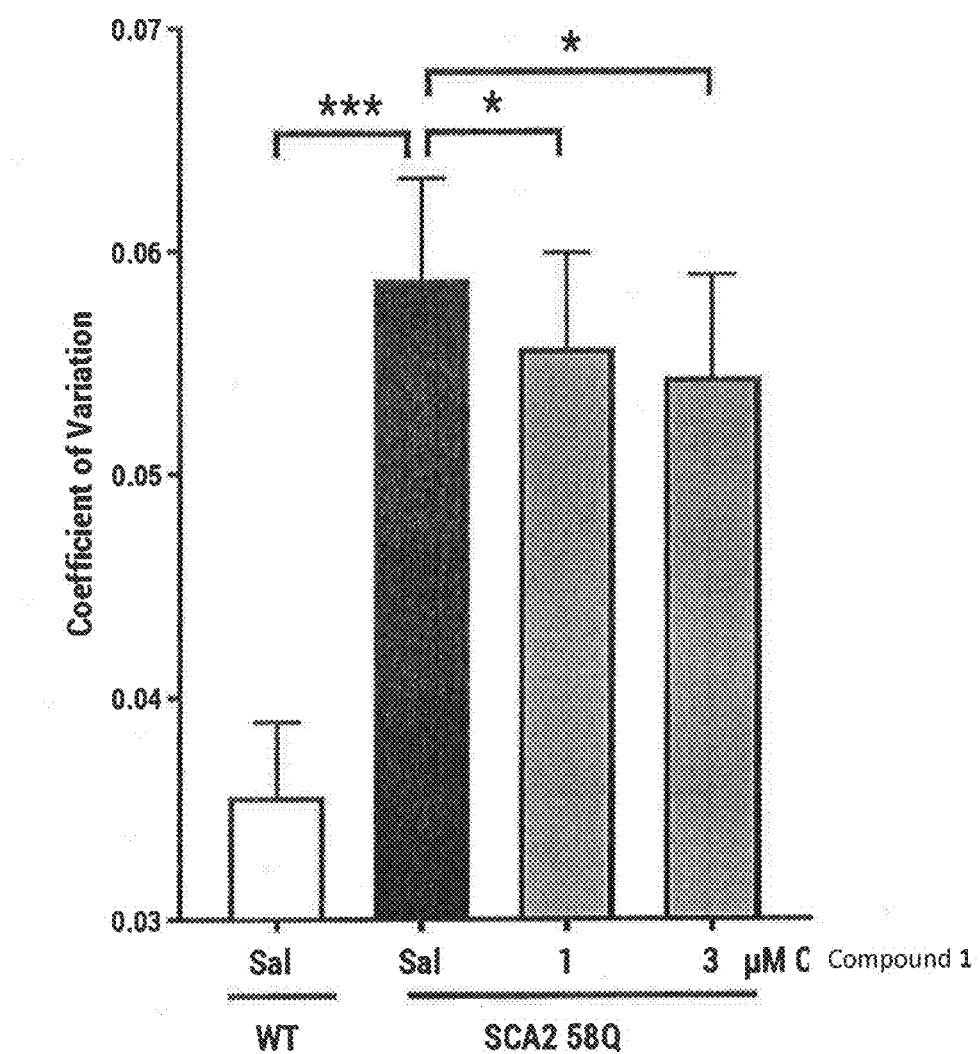
FIG. 3 shows the effects of Compound 1 on Purkinje cell firing irregularity in ex vivo slices from SCA2 58Q transgenic mice.

Effect on Purkinje Cell Firing Irregularity in Ex Vivo Slices from SCA2 58Q Transgenic Mice In cerebellar slices from SCA2 58Q mice, Purkinje neurons exhibit chaotic firing, measurable as an increase in the coefficient of variation of the interspike interval (ISI CV), a measure of the regularity of the firing interval between action potentials. The difference in ISI CV between wild-type (N=8) and SCA2 58Q (N=11) mice is illustrated in FIG. 3 ($P<0.005$). Also shown, sequential bath application of 1 (N=11) or 3 µM (N=10) Compound 1 partially reversed the increase in ISI CV observed in cerebellar slices from eleven-month old SCA2 58Q mice ($P<0.05$). These data indicate that Compound 1 regularizes Purkinje firing by partially restoring the interspike interval in this mouse model of Spinocerebellar Ataxia.

Figure 4:
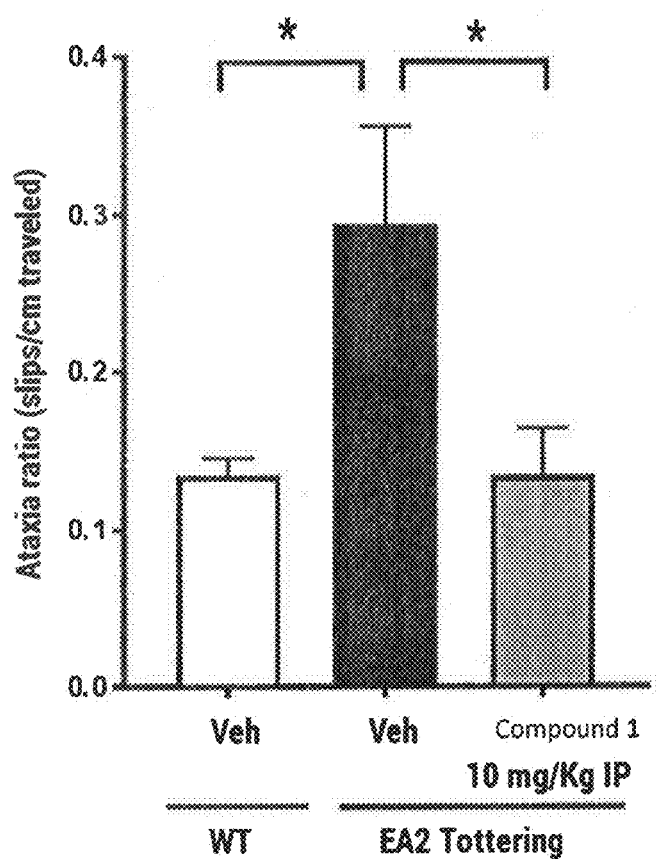
FIG. 4 shows the effects of Compound 1 on baseline ataxia in the EA2 Tottering mouse model.

Evaluation of Compound Effect in Episodic Ataxia 2 (EA2) Tottering Mouse Model Compound 1 has demonstrated efficacy in validated animal models of hereditary ataxia (EA2) and ET (harmaline-induced tremor). To test whether Compound 1 can alleviate ataxia in a disease model, it was evaluated in the EA2 "Tottering" mouse model. These mice display a basal ataxia that arises from irregularity in Purkinje cell pacemaker firing due to a loss-of-function mutation in P/Q $Ca^{2+}$ channels (the same protein that is mutated in SCA6), which causes Episodic Ataxia 2 (EA2). Animals were assessed in the parallel rod floor apparatus which automatically counts the number of times the animal's foot slips through the evenly spaced metal rods and the total distance the animal travels. Baseline ataxia was then expressed as the Ataxia Ratio, which is the total number of foot slips divided by the total distance the animal travels in centimeters. The increase in Ataxia Ratio between wild-type and EA2 mice is illustrated in FIG. 4.

In this study, EA2 (8-10 months old; n=18) mice were injected intraperitoneally with Compound 1 or vehicle 30 minutes prior to being placed in the parallel rod floor apparatus. Animals were assessed in a cross-over study design with each animal receiving both vehicle and 10 mg/kg Compound 1. Three days were allowed between doses for washout of the compound. At the dose administered in this study, Compound 1 fully reversed the increase in Ataxia Ratio observed in EA2 vs wild-type mice. These data indicate that Compound 1 restores normal performance in this measure of motor function in a model of hereditary cerebellar ataxia.

Comparative Advantages

The following studies illustrate further technical advantages of the compounds disclosed herein.

Aqueous solubility (kinetic solubility) tests of the compounds were performed in phosphate buffer saline (pH 7.4) measured by shake-flask method. In this assay, DMSO stock solution of test compound is added to buffer followed by equilibration (shaking), filtration and determination of soluble amount by HPLC-UV Conditions used in the assay are summarized below. Results are shown in Table 2 and Table 3.
   Compound concentration: 200 µM with 1% DMSO (n=2)
   Aqueous buffer: 0.05M Phosphate Buffer System pH 7.4
   Equilibration period: 16 hours at room temperature (~23° C.) with agitation
   Sample preparation: Filtration
   Analysis: HPLC-UV
   Reference compounds: Caffeine (high solubility) and Diethylstilbestrol (low solubility)

Metabolic stability profiling of the compounds was performed in liver microsomes. In this assay, test compound is incubated with liver microsomes in the presence of NADPH for 2 time points at 37° C. At the end of incubation, reaction is quenched with acetonitrile containing internal standard and the parent compound remaining is determined by LC-MS/MS. Conditions used in the assay are summarized below. Results are shown in Table 2.
   Incubation time: 0 and 30 minutes at pH 7.4, 37° C.
   Test concentration: 1 µM in 0.02% DMSO at pH 7.4 (n=2)
   NADPH concentration in assay: 1 mM
   Liver microsome protein concentration in assay: 0.5 mg/ml
   Analysis: LC-MS/MS
   Data reported: % Parent Compound Remaining (% PCR)
   Reference compounds for high and low clearance are included
   Species tested: mouse, rat, dog, monkey, and human Compounds described herein were tested for CYP inhibition across 5 isoforms (3A4, 2D6, 2C9, 2C19 & 1A2). In this assay, CYP isoform specific substrates are incubated with human liver microsome (HLM) in the presence of test compounds, and metabolite formation is determined. Percentage inhibition of metabolite formation at different concentrations of test compound is calculated and $IC_{50}$ is determined. Conditions used in the assay are summarized below. Results are shown in Table 2.
   Test drug (Inhibitor) Concentration: 8 different concentrations (100 µM to 0.005 µM)
   Matrix: Human Liver Microsome (Invitrogen, life technologies)
   Specific probe substrates will be used for the isoforms as given below:
   CYP3A4: Midazolam
   CYP2D6: Bufuralol
   CYP2C9: Diclofenac
   CYP2C19: Mephynitoin
   CYP1A2: Phenacetin
   Cofactors: NADPH (1 mM final in assay)
   Sample Analysis: LC-MS/MS (metabolites)
   Specific reference inhibitors included in all assays (Ketoconazole/Quinidine/Sulphaphenazole/Ticlopidine/Furafylline)
   Buffer: Potassium Phosphate Buffer (100 mM) pH 7.4
   DMSO level in assay: 0.1%
   Data analysis: % Inhibition over control Compounds were tested in a cardiac potassium channel hERG assay. hERG is responsible for a rapid delayed rectifier current ($I_{Kr}$) in human ventricles. Inhibition of $I_{Kr}$ is the most common cause of cardiac action potential prolongation by non-cardiac drugs. See e.g., Brown, A. M. and Rampe, D. (2000). Drug-induced long QT syndrome: is HERG the root of all evil? Pharmaceutical News 7, 15-20.

HEK-293 cells were stably transfected with hERG cDNA. Stable transfectants were selected by coexpression with the G418-resistance gene incorporated into the expression plasmid. Selection pressure was maintained by including G418 in the culture medium. Cells were cultured in Dulbecco's Modified Eagle Medium/Nutrient Mixture F-12 (D-MEM/F-12) supplemented with 10% fetal bovine serum, 100 U/mL penicillin G sodium, 100 µg/mL streptomycin sulfate and 500 µg/mL G418. Cell culture records are kept on file at Charles River Laboratories.

Cells were transferred to the recording chamber and superfused with vehicle control solution. Pipette solution for whole cell recordings was (composition in mM): potassium aspartate, 130; $MgCl_2$, 5; EGTA, 5; ATP, 4; HEPES, 10; pH adjusted to 7.2 with KOH. Pipette solution was prepared in batches, aliquoted, stored frozen, and a fresh aliquot thawed each day. Patch pipettes were made from glass capillary tubing using a P-97 micropipette puller (Sutter Instruments, Novato, Calif.). A commercial patch clamp amplifier was used for whole cell recordings. Before digitization, current records were low-pass filtered at one-fifth of the sampling frequency.

Onset and steady state inhibition of hERG current was measured using a pulse pattern with fixed amplitudes (conditioning prepulse: +20 mV for 2 s; test pulse: −50 mV for 2 s) repeated at 10 s intervals, from a holding potential of −80 mV. Peak tail current was measured during the 2 s step to −50 mV.

One test article concentration was applied to each cell (n=3). Peak current was measured during the test ramp. A steady state was maintained for at least 30 seconds before applying test article or positive control. Peak current was measured until a new steady state was achieved. Results are shown in Table 2.

Oral bioavailability data was collected in rat as follows. Results are shown in Table 2.

Rat strain/sex: Sprague Dawley/Male
Age/body weight: 6 to 8 weeks/250-300 gms
No of animals per group: n=3
Total no of groups: 2 (1 mpk IV & 10 mpk PO)
Route of administration: Oral (PO)/Intravenous (IV)
Dosing volume: Intravenous (2 ml/kg) & Oral (10 ml/kg)
Formulation vehicles: Standard formulations or suggested by Sponsor Dose levels (IV & Oral): 1 mg/kg; intravenous & 10 mg/kg; oral or as suggested
Fast/Fed: Oral dosing will be performed with overnight fasted animal Dosing frequency: Single dose
Time points for blood collection: (57 plasma samples for analysis) IV—10 points (pre-dose; 5 min; 15 min; 30 min; 1 h; 2 h; 4 h; 6 h; 8 h; 24 h) [n=3 rats]
PO—9 points (pre-dose; 15 min; 30 min; 1 h; 2 h; 4 h; 6 h; 8 h; 24 h) [n=3 rats]
Blood samples collection: Jugular vein cannula
Anti-coagulant: 0.2% K2 EDTA
Sample analysis by discovery grade bioanalytical method developed for estimation of test compound in plasma using LC-MS/MS systems.

TABLE 2

| | Compound 1 | Comparator A | Comparator B |
|---|---|---|---|
| SK2 potency ($SC_{100}$)[a] | 400 nM | 1380 nM | 5800 nM |
| Brain Free Fraction[a] | 6.1% | 1.2% | NA |
| Kinetic solubility (mg/mL) | 0.074 | 0.017 | NA |
| Liver microsome stability[†] Mouse | 47% | 1% | NA |
| Rat | 60% | 1% | NA |
| Dog | 54% | 2% | NA |
| Monkey | 46% | 1% | NA |
| Human | 84% | 50% | NA |
| Cyp1A2 inhibition ($IC_{50}$) | >10 uM | 640 nM | NA |
| Cyp3A4 inhibition ($IC_{50}$) | >10 uM | >10 uM | NA |
| Cyp2D6 inhibition ($IC_{50}$) | >10 uM | 790 nM | NA |
| hERG inhibition ($IC_{50}$) | >10 uM | >10 uM | NA |
| Oral bioavailability[§] | 81% | 5% | NA |

$SC_{100}$ = Concentration that produces doubling of channel current
[a]Small discrepancy in number when compared with prior table due to insignificant differences in averages taken from later experiments.
[†]% remaining at 1 hour
[§]10 mg/kg PO, 0.5 mg/kg IV in rat As shown by the data in Table 2 above, Compound 1 is over 3-fold more potent on SK2 then Comparator A and over 14-fold more potent on SK2 then Comparator B. Compound 1 also has better solubility, higher BFF, higher microsomal stability, and greater oral bioavailability than Comparator A. An overall improvement in BFF and solubility over Comparator A and phenyl derivative Comparator C was also demonstrated across the compounds described herein as shown in Table 3. Compound 1 is reproduced from above for ease of comparison.

TABLE 3

| Structure | Brain Free Fraction | Kinetic solubility (mg/mL) |
|---|---|---|
| 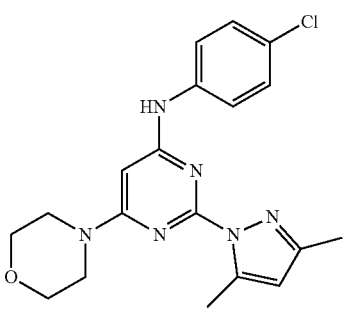 [SMILES: Cc1cc(C)n(-c2nc(Nc3ccc(Cl)cc3)cc(N3CCOCC3)n2)n1] Comparator C | 0.16% | 0.001 |
| 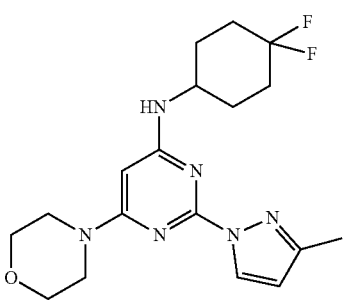 [SMILES: Cc1ccn(-c2nc(NC3CCC(F)(F)CC3)cc(N3CCOCC3)n2)n1] Compound 1 | 6.1% | 0.074 |
| 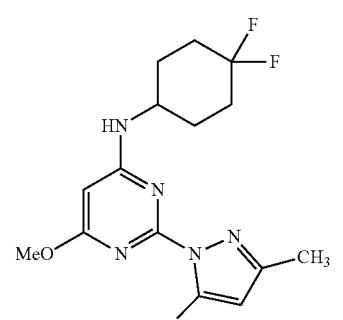 Compound 2 | 2.76% | 0.031 |
| 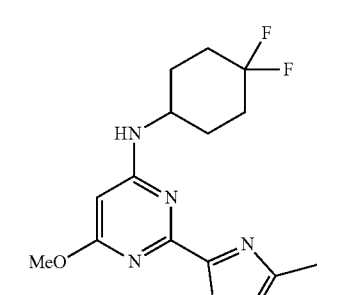 Compound 3 | 2.69% | 0.0709 |
| 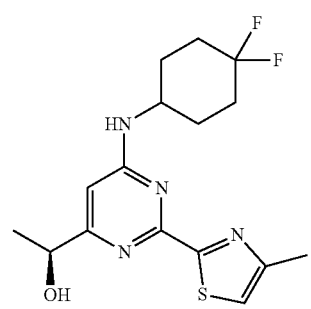 [SMILES: Cc1csc(-c2nc(NC3CCC(F)(F)CC3)cc([C@H](C)O)n2)n1] Compound 5 | 4.20% | 0.0803 |
| 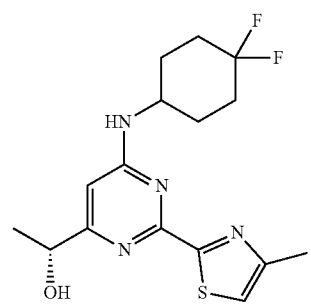 [SMILES: Cc1csc(-c2nc(NC3CCC(F)(F)CC3)cc([C@@H](C)O)n2)n1] Compound 6 | 4.31% | 0.0667 |
| 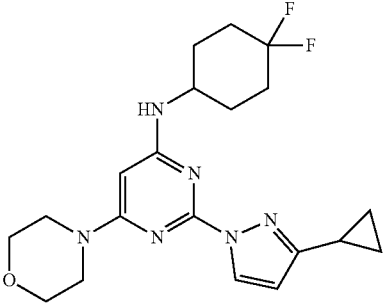 [SMILES: FC1(F)CCC(Nc2cc(N3CCOCC3)nc(-n3ccc(C4CC4)n3)n2)CC1] Compound 7 | 1.55% | 0.0497 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A method of treating a disease or condition selected from ataxia, dystonia, tremors, Parkinson's disease, ischemia, traumatic brain injury, amyotrophic lateral sclerosis, hypertension, atherosclerosis, diabetes, arrhythmia, overactive bladder, anxiety, epilepsy, insomnia, and withdrawal symptoms caused by the termination of abuse of alcohol and other drugs of abuse in a subject in need thereof comprising the step of administering to the subject a compound of the formula:

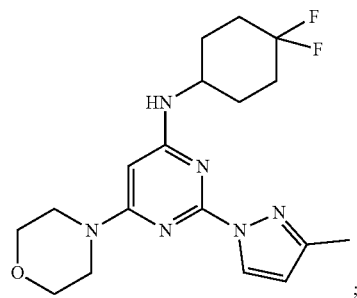 [SMILES: Cc1ccn(-c2nc(NC3CCC(F)(F)CC3)cc(N3CCOCC3)n2)n1]

or a pharmaceutically acceptable salt thereof.

2. The method of claim 1, wherein the disease or condition is anxiety.

3. The method of claim 1, wherein the disease or condition is Parkinson's disease.

4. A method of treating essential tremor in a subject in need thereof comprising the step of administering to the subject a compound of the formula:

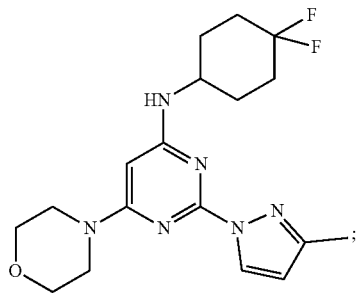 [SMILES: Cc1ccn(-c2nc(NC3CCC(F)(F)CC3)cc(N3CCOCC3)n2)n1]

or a pharmaceutically acceptable salt thereof.

5. A method of treating ataxia in a subject in need thereof comprising the step of administering to the subject a compound of the formula:

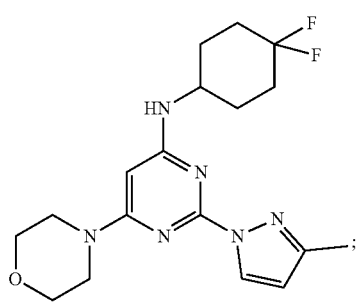 [SMILES: Cc1ccn(-c2nc(NC3CCC(F)(F)CC3)cc(N3CCOCC3)n2)n1]

or a pharmaceutically acceptable salt thereof.

6. The method of claim 5, wherein the ataxia is spinocerebellar ataxia.

* * * * *